(12) United States Patent
Guevremont et al.

(10) Patent No.: US 7,026,612 B2
(45) Date of Patent: Apr. 11, 2006

(54) FAIMS APPARATUS AND METHOD USING CARRIER GASES THAT CONTAIN A TRACE AMOUNT OF A DOPANT SPECIES

(75) Inventors: Roger Guevremont, Ottawa (CA); Randy Purves, Orleans (CA); David Barnett, Orleans (CA); Barbara Ells, Orleans (CA)

(73) Assignee: Ionalytics Corporation, Ottawa (CA)

( * ) Notice: Subject to any disclaimer, the term of this patent is extended or adjusted under 35 U.S.C. 154(b) by 0 days.

(21) Appl. No.: 10/503,713

(22) PCT Filed: Feb. 7, 2003

(86) PCT No.: PCT/CA03/00171

§ 371 (c)(1),
(2), (4) Date: Aug. 6, 2004

(87) PCT Pub. No.: WO03/067237

PCT Pub. Date: Aug. 14, 2003

(65) Prior Publication Data
US 2005/0161596 A1   Jul. 28, 2005

Related U.S. Application Data

(60) Provisional application No. 60/354,711, filed on Feb. 8, 2002.

(51) Int. Cl.
*H01J 49/40* (2006.01)

(52) U.S. Cl. .................. 250/288; 250/286; 250/281; 250/282

(58) Field of Classification Search ............. 250/288, 250/286, 281, 282, 287
See application file for complete search history.

(56) References Cited

U.S. PATENT DOCUMENTS

| | | | |
|---|---|---|---|
| 3,668,383 A | 6/1972 | Carroll | |
| 4,311,669 A | 1/1982 | Spangler | |
| 5,106,468 A | 4/1992 | Chimenti | |
| 5,283,199 A * | 2/1994 | Bacon et al. | 436/173 |
| 5,420,424 A | 5/1995 | Carnahan et al. | |
| 5,455,417 A | 10/1995 | Sacristan | |
| 5,723,861 A | 3/1998 | Carnahan et al. | |

(Continued)

OTHER PUBLICATIONS

Mason et al., "Transport Properties of Ions in Gases", (1988), Wiley, New York.

(Continued)

*Primary Examiner*—Nikita Wells
(74) *Attorney, Agent, or Firm*—Freedman & Associates

(57) ABSTRACT

Disclosed is a method and apparatus for improving at least one of a peak separation and a signal intensity relating to an ion of interest being transmitted through an analyzer region of a FAIMS apparatus. A method according to the instant invention includes a step of introducing ions including an ion of interest into an analyzer region of a FAIMS. A flow of a doped carrier gas other than air is also provided through the analyzer region. The doped carrier gas includes a carrier gas and a trace amount of a predetermined dopant gas, the predetermined dopant gas selected for improving at least one of a peak separation and a signal intensity relating to the ion of interest relative to the peak separation and the signal intensity relating to the ion of interest in the presence of the carrier gas only. The ion of interest is selectively transmitted through the analyzer region in the presence of the doped carrier gas, and detected at a detector.

38 Claims, 14 Drawing Sheets

U.S. PATENT DOCUMENTS

| | | | |
|---|---|---|---|
| 5,736,739 | A | 4/1998 | Uber et al. |
| 5,763,876 | A | 6/1998 | Pertinarides et al. |
| 5,869,831 | A | 2/1999 | De La Mora et al. |
| 6,495,823 | B1 | 12/2002 | Miller et al. |
| 6,504,149 | B1 | 1/2003 | Guevremont et al. |
| 6,512,224 | B1 * | 1/2003 | Miller et al. ............... 250/286 |
| 6,559,441 | B1 | 5/2003 | Clemmer |
| 6,621,077 | B1 | 9/2003 | Guevremont et al. |
| 6,639,212 | B1 | 10/2003 | Guevremont et al. |
| 6,690,004 | B1 | 2/2004 | Miller et al. |
| 6,774,360 | B1 * | 8/2004 | Guevremont et al. ....... 250/288 |
| 6,787,765 | B1 * | 9/2004 | Guevremont et al. ....... 250/288 |
| 2003/0057369 | A1 | 3/2003 | Guevremont et al. |

OTHER PUBLICATIONS

Buryakov et al., "A New Method of Separation of Multi-Atomic Ions by Mobility at Atmospheric Pressure using a High-Frequency Amplitude-Asymmetric Strong Electric Field", Int. J. Mass Spectrom. Ion Processes, No. 128, pp. 143-148, (1993), Elsevier Science Publishers B.V.

Eiceman et al., "Ion Mobility Spectrometry", (1994), CRC Press, Florida.

Carnahan et al., "Field Ion Spectrometry—A New Analytical Technology for Trace Gas Analysis", Proceedings of the 41st Annual ISA Analysis Division Symposium, paper#96-009, pp. 87-95, (1996), Framingham, MA, USA.

Guevremont et al., "Combined Ion Mobility/Time-of-Flight Mass Spectrometry Study of Electrospray-Generated Ions", Anal. Chem. 1997, vol. 69, No. 19, pp. 3959-3965, (Oct. 1, 1997), American Chemical Society.

Hudgins et al., "High Resolution Ion Mobility Measurements for Gas Phase Proteins: Correlation beteen Solution Phase and Gas Phase Conformations", Int. J. of Mass Spec. and Ion Processes 165/166, pp. 497-507, (1997), Elsevier Science Publishers B.V.

Riegner et al., "Qualitative Evaluation of Field Ion Spectrometry for Chemical Warfare Agent Detection", Proceedings of the 45th ASMS Conference on Mass Spectrometry and Allied Topics, Palm Springs, California, pp. 473, (1997).

Purves et al., "Mass Spectrometric Characterization of a High-Field Asymmetric Waveform Ion Mobility Spectrometer", Review of Scientific Instruments, vol. 69, No. 12, pp. 4094-4105, (Dec. 1998), American Institute of Physics.

Henderson et al., "ESI/Ion Trap/Ion Mobility/Time-of-Flight Mass Spectrometry for Rapid and Sensitive Analysis of Biomolecular Mixtures", Anal. Chem. 1999, vol. 71, No. 2, pp. 291-301, (Jan. 15, 1999), American Chemical Society.

Guevremont et al., "Atmospheric Pressure Ion Focusing in a High-Field Asymmetric Waveform Ion Mobility Spectrometer", Review of Scientific Instruments, vol. 70, No. 2, pp. 1370-1383, (Feb. 1999), American Institute of Physics.

Purves et al., "Elongated conformers of charge states +11 to +15 of bovine ubiquitin studied using ESI-FAIMS-MS", J.Am.Soc.Mass.Spectrom., vol. 12, No. 8, Aug. 2001, pp. 894-901, Elsevier Science Inc., New York, NY, US.

* cited by examiner

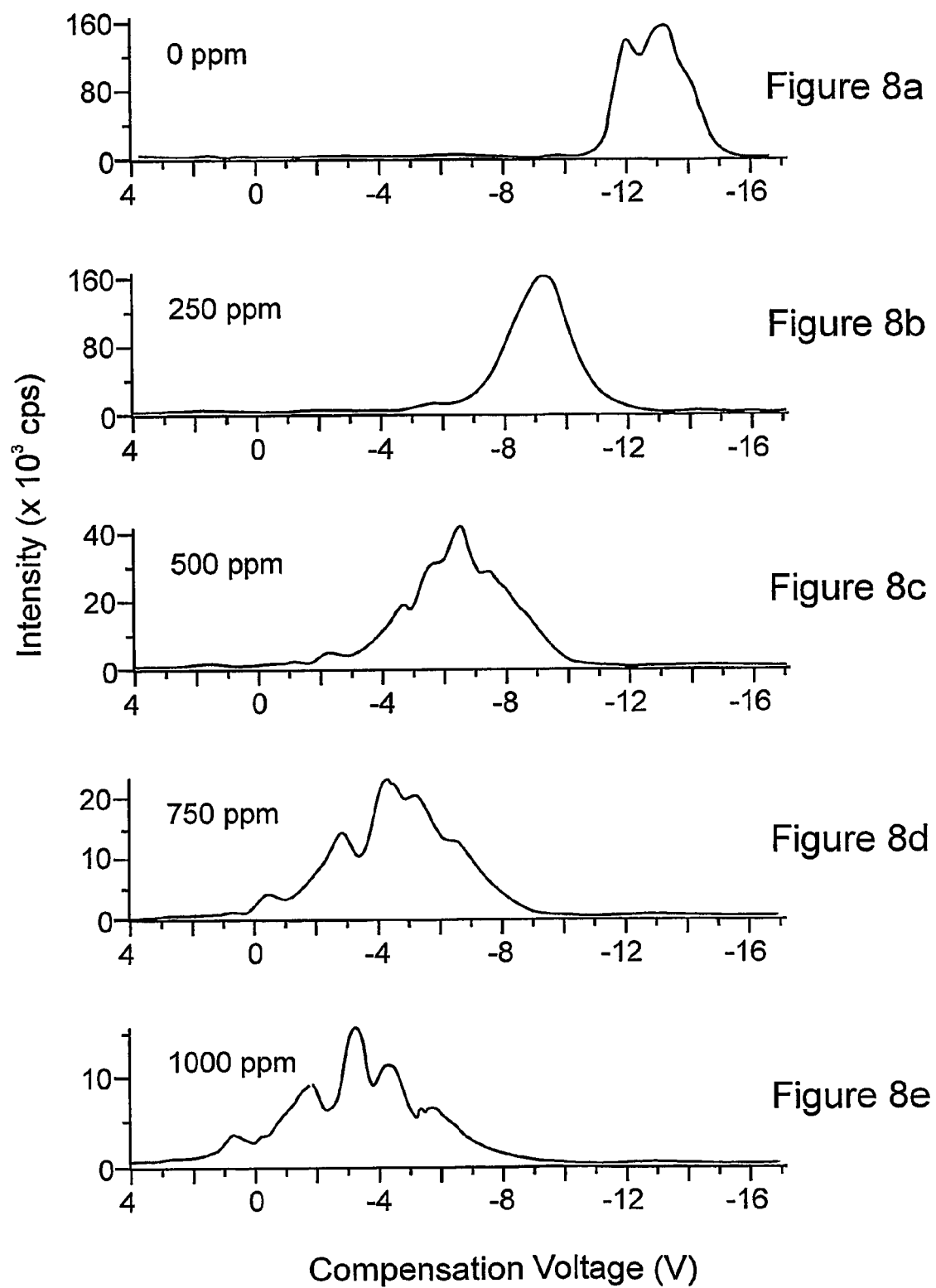

Compensation Voltage (V)

Compensation Voltage (V)

FAIMS APPARATUS AND METHOD USING CARRIER GASES THAT CONTAIN A TRACE AMOUNT OF A DOPANT SPECIES

This application claims the benefit of U.S. Provisional Application No. 60/354,711, filed Feb. 8, 2002.

FIELD OF THE INVENTION

The instant invention relates generally to high field asymmetric waveform ion mobility spectrometry (FAIMS), more particularly the instant invention relates to an apparatus and method for selectively transmitting ions according to the FAIMS principle using carrier gases that contain a trace amount of a dopant species.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative-cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

U.S. Pat. No. 5,420,424, issued to Carnahan and Tarassov on May 30, 1995, teaches a FAIMS device having cylindrical electrode geometry and electrometric ion detection, the contents of which are incorporated herein by reference. The FAIMS analyzer region is defined by an annular space between inner and outer cylindrical electrodes. In use, ions that are to be separated are entrained into a flow of a carrier gas and are carried into the analyzer region via an ion inlet orifice. Once inside the analyzer region, the ions become distributed all the way around the inner electrode as a result of the carrier gas flow and ion-ion repulsive forces. The ions are selectively transmitted within the analyzer region to an ion extraction region at an end of the analyzer region opposite the ion inlet end. In particular, a plurality of ion outlet orifices is provided around the circumference of the outer electrode for extracting the selectively transmitted ions from the ion extraction region for electrometric detection. Of course, the electrometric detectors provide a signal that is indicative of the total ion current arriving at the detector. Accordingly, the CV spectrum that is obtained using the Carnahan device does not include information relating to an identity of the selectively transmitted ions. It is a limitation of the Carnahan device that the peaks in the CV spectrum are highly susceptible to being assigned incorrectly.

Replacing the electrometric detector with a mass spectrometer detection system provides an opportunity to obtain additional experimental data relating to the identity of ions giving rise to the peaks in a CV spectrum. For instance, the mass-to-charge (m/z) ratio of ions that are selectively transmitted through the FAIMS at a particular combination of CV and DV can be measured. Additionally, replacing the mass spectrometer with a tandem mass spectrometer makes it possible to perform a full-fledged structural investigation of the selectively transmitted ions. Unfortunately, the selectively transmitted ions are difficult to extract from the analyzer region of the Carnahan device for subsequent detection by a mass spectrometer. In particular, the orifice plate of a mass spectrometer typically includes a single small sampling orifice for receiving ions for introduction into the mass spectrometer. This restriction is due to the fact that a mass spectrometer operates at a much lower pressure than the FAIMS analyzer. In general, the size of the sampling orifice into the mass spectrometer is limited by the pumping efficiency of the mass spectrometer vacuum system. In principle, it is possible to align the sampling orifice of a mass spectrometer with a single opening in the FAIMS outer electrode of the Carnahan device; however, such a combination suffers from very low ion transmission efficiency and therefore poor detection limits. In particular, the Carnahan device does not allow the selectively transmitted ions to be concentrated for extraction through the single opening. Accordingly, only a small fraction of the selectively transmitted ions are extracted from the analyzer region, the vast majority of the selectively transmitted ions being neutralized eventually upon impact with an electrode surface.

Guevremont et al. describe the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region between the cylindrical electrodes as a result of the electric fields which change with radial distance. Focusing the ions of interest has the effect of reducing the number of ions of interest that are lost as a result of the ion suffering a collision with one of the inner and outer electrodes.

In WO 00/08455, the contents of which are incorporated herein by reference, Guevremont and Purves describe an improved tandem FAIMS/MS device, including a domed-FAIMS analyzer. In particular, the domed-FAIMS analyzer includes a cylindrical inner electrode having a curved surface terminus proximate the ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, except that the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ion cloud to travel towards the ion-outlet orifice, which advantageously also prevents the ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned tandem FAIMS/MS device, which achieves ion transmission from the domed-FAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a smaller orifice leading into the vacuum system of the mass spectrometer. Accordingly, such tandem FAIMS/MS devices are highly sensitive instruments that are capable of detecting and identifying ions of interest at part-per-billion levels.

The prior art FAIMS devices typically use a carrier gas comprising a purified flow of one of nitrogen, oxygen and air. For instance, Carnahan and Tarassov in U.S. Pat. No. 5,420,424 teach the use of dehumidified air as the carrier gas. In WO 00/08455, Guevremont and Purves teach providing a compressed gas, such as for instance one of air and nitrogen, which is passed through a charcoal/molecular sieve gas purification cylinder before being introduced into the analyzer region of a FAIMS device.

In Rev. Sci. Instrum., Vol. 69, No. 12, December 1998, the contents of which are herein incorporated by reference, Purves et al. report results that were obtained through experimentation and which illustrate the deleterious effects of having concomitant compounds in the carrier gas stream. In particular, Purves et al. reported that the CV spectra obtained when the FAIMS device was operated at elevated temperature are dramatically different than corresponding CV spectra obtained prior to elevating the temperature. It was hypothesized that water molecules and other contaminants were being desorbed from the various internal surfaces of the FAIMS device as the temperature was raised. Subsequent interactions between the ions of interest, in these experiments positive ions, and the desorbed species resulted in significant suppression of the detector signal when the FAIMS device was operated in a mode in which the polarity of the dispersion voltage is positive (P1). Purves et al. state that the P1 mode is very sensitive to gas phase impurities. Conversely, a dramatic increase of the detector signal of the positive ions was observed under similar operating conditions when the FAIMS device was operated in a mode in which the polarity of the dispersion voltage is negative (P2). Purves et al. suggest that several of the impurities are observed in the P2 CV spectrum, which is in keeping with an initial increase in the total ion intensity as the various internal surfaces are heated and the contaminant species are desorbed therefrom. Purves et al. do not suggest that the presence of a small amount of water or another contaminant in the carrier gas stream could be used to improve the results that are obtained using FAIMS. Rather, they indicate that their preliminary results suggest that the high sensitivity of FAIMS to concomitant compounds in the gas stream and high sensitivity to changes in analyte concentration will introduce difficulty in identification of ions by FAIMS. This view is reiterated by the same authors in Rev. Sci. Instrum. Vol. 70, No. 2, February 1999, the contents of which are herein incorporated by reference.

In WO 01/69646, the contents of which are herein incorporated by reference, Guevremont et al. describe in detail the effect of using gas mixtures to change the separation capabilities and signal intensity of ions transmitted through a FAIMS device. It was found that the behavior of ions in these gas mixtures is not predictable based upon the behavior of the ions in the individual gases in the mixture. This unexpected behavior led to unforeseen advantages for the analyses of several ions using a FAIMS device. However, the amount of each gas that was used to induce a change was always in excess of one percent. Furthermore, many types of ions do not display such advantageous behavior in the types of gas mixtures that were described in WO 01/69646.

It would be advantageous to provide a method and an apparatus for separating ions according to the FAIMS principle that overcomes the limitations of the prior art.

SUMMARY OF THE INVENTION

In accordance with an aspect of the invention there is provided an apparatus for selectively transmitting ions comprising: a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting an ion of interest at a given combination of asymmetric waveform voltage and compensation voltage; and, a doping portion for receiving a flow of a carrier gas from a gas source and for controllably mixing a dopant gas with the flow of a carrier gas to produce a doped carrier gas stream containing a predetermined concentration of the dopant gas, the doping portion also in fluid communication with the analyzer region for providing the doped carrier gas stream thereto, wherein during use the doped carrier gas stream that is provided to the analyzer region contains less than 1% dopant gas by volume.

In accordance with another aspect of the invention there is provided an apparatus for selectively transmitting ions comprising: a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting an ion of interest at a given combination of asymmetric waveform voltage and compensation voltage; a carrier gas source for providing a flow of a carrier gas; a first containing portion for containing a first gas mixture including a first concentration of a dopant gas; a second containing portion for containing a second gas mixture including a second concentration of the dopant gas; and, a doping portion in fluid communication with the carrier gas source, the first containing portion, the second containing portion and the analyzer region, for receiving the flow of a carrier gas from the gas source and for controllably mixing at least one of the first gas mixture and the second gas mixture with the flow of the carrier gas, to form a doped carrier gas stream containing a predetermined concentration of the dopant gas, and for providing the doped carrier gas stream to the analyzer region, wherein during use the doped carrier gas stream that is provided to the analyzer region contains less than 1% dopant gas by volume.

In accordance with another aspect of the invention there is provided a method of selectively transmitting ions, comprising the steps of: introducing ions including an ion of interest into an analyzer region of a high field asymmetric waveform ion mobility spectrometer; providing a flow of a doped carrier gas other than air through the analyzer region, the doped carrier gas including a carrier gas and a trace amount of a predetermined dopant gas, the predetermined dopant gas selected for improving at least one of a peak separation and a signal intensity relating to the ion of interest relative to the peak separation and the signal intensity relating to the ion of interest in the presence of the carrier gas only; and, selectively transmitting the ion of interest through the analyzer region in the presence of the doped carrier gas.

In accordance with another aspect of the invention there is provided a method of selectively transmitting ions, comprising the steps of: providing an analyzer region defined by a space between two spaced-apart electrodes; providing an electric field within the analyzer region resulting from the application of an asymmetric waveform voltage to at least one of the two electrodes and from the application of a direct-current compensation voltage to at least one of the two electrodes; providing a flow of a carrier gas from a carrier gas source; removing water vapour from the flow of a carrier gas to provide a flow of a dried carrier gas; adding a trace amount of a predetermined dopant gas to the flow of a dried carrier gas to provide a flow of a doped carrier gas; introducing the flow of a doped carrier gas into the analyzer region; introducing ions including an ion of interest into the analyzer region; and selectively transmitting the ion of interest through the analyzer region in the presence of the doped carrier gas.

In accordance with another aspect of the invention there is provided a method of selectively transmitting ions, comprising the steps of: providing an analyzer region defined by a space between two spaced-apart electrodes; providing an electric field within the analyzer region resulting from the application of an asymmetric waveform voltage to at least one of the two electrodes and from the application of a direct-current compensation voltage to at least one of the two electrodes; determining a suitable dopant gas for improving one of a peak separation and a signal intensity relating to an ion of interest; providing a flow of a carrier gas other than air through the analyzer region, the carrier gas including a first gas and a trace amount of the suitable dopant gas; introducing ions including the ion of interest into the analyzer region; and, selectively transmitting the ion of interest through the analyzer region.

BRIEF DESCRIPTION OF THE DRAWINGS

Exemplary embodiments of the invention will now be described in conjunction with the following drawings, in which similar reference numbers designate similar items:

FIG. 8a shows a CV spectrum for the +5 charge state of bovine insulin when a purified carrier gas stream is used;

FIG. 8b shows a CV spectrum for the +5 charge state of bovine insulin when 250 ppm of 2-chlorobutane is added to the carrier gas stream;

FIG. 8c shows a CV spectrum for the +5 charge state of bovine insulin when 500 ppm of 2-chlorobutane is added to the carrier gas stream;

FIG. 8d shows a CV spectrum for the +5 charge state of bovine insulin when 750 ppm of 2-chlorobutane is added to the carrier gas stream;

FIG. 8e shows a CV spectrum for the +5 charge state of bovine insulin when 1000 ppm of 2-chlorobutane is added to the carrier gas stream;

DETAILED DESCRIPTION OF THE DRAWINGS

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
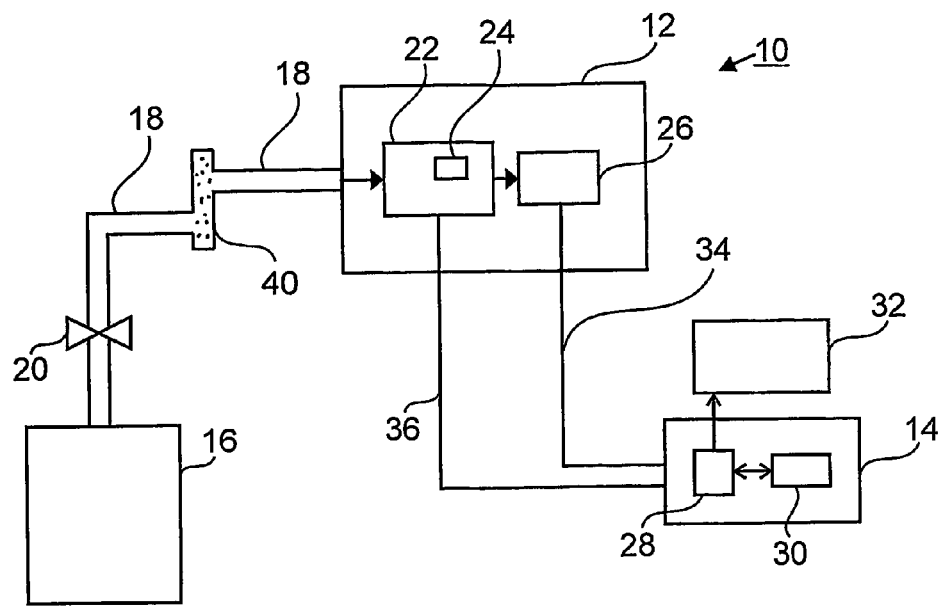
FIG. 1 is a simplified block diagram of a FAIMS apparatus according to the prior art.

Referring to FIG. 1, shown is a FAIMS apparatus according to the prior art. The apparatus, shown generally at 10, includes an analyzer portion 12, a control portion 14 and a gas source portion 16. The gas source portion 16 is in fluid communication with the analyzer portion via a gas transfer line 18. A flow controller or valve 20 is disposed at a point along the length of the gas transfer line 18 for adjusting a flow rate of a gas from the gas source portion 16. The analyzer portion 12 includes a high field asymmetric waveform ion mobility spectrometer (FAIMS) 22. For instance, the FAIMS 22 is in the form of one of a cylindrical geometry domed-FAIMS, a side-to-side FAIMS and a parallel plate FAIMS. An ionization source 24 is provided in communication with the FAIMS 22 for providing sample ions thereto. During use, the ions of interest are transmitted through the FAIMS 22 and detected. For instance, the ions of interest are extracted from the FAIMS 22 for introduction into a mass spectrometer 26. The mass spectrometer 26 provides an electrical signal, which is proportional to a measured ion current of the transmitted ions, to the control portion 14 via a first communication line 34. For instance, the control portion 14 is a micro-computer including a processor 28 and a memory 30. The control portion 14 is in electrical communication with a display device 32, for providing information to a user of the apparatus 10. The control portion 14 is also in electrical communication with the FAIMS 22 via a second communication line 36 for controlling the application of an asymmetric waveform voltage and a direct current compensation voltage to not illustrated electrodes of the FAIMS 22.

Referring still to FIG. 1, the apparatus 10 further includes a gas filter, for instance a charcoal/molecular sieve filter 40, which is disposed at a point along the gas transfer line 18 intermediate the gas source portion 16 and the analyzer portion 12. The purpose of the gas filter is to remove traces of water and/or other contaminants from the gas that is provided from the gas source portion 16. As discussed supra, the prior art teaches that the presence of concomitant compounds in the gas stream leads to a decrease in at least one of the separation capability, reproducibility, and the sensitivity of FAIMS. Accordingly, the prior art FAIMS devices are operated under carefully controlled conditions whereby such contaminants are absent within the FAIMS analyzer region.

Figure 2:
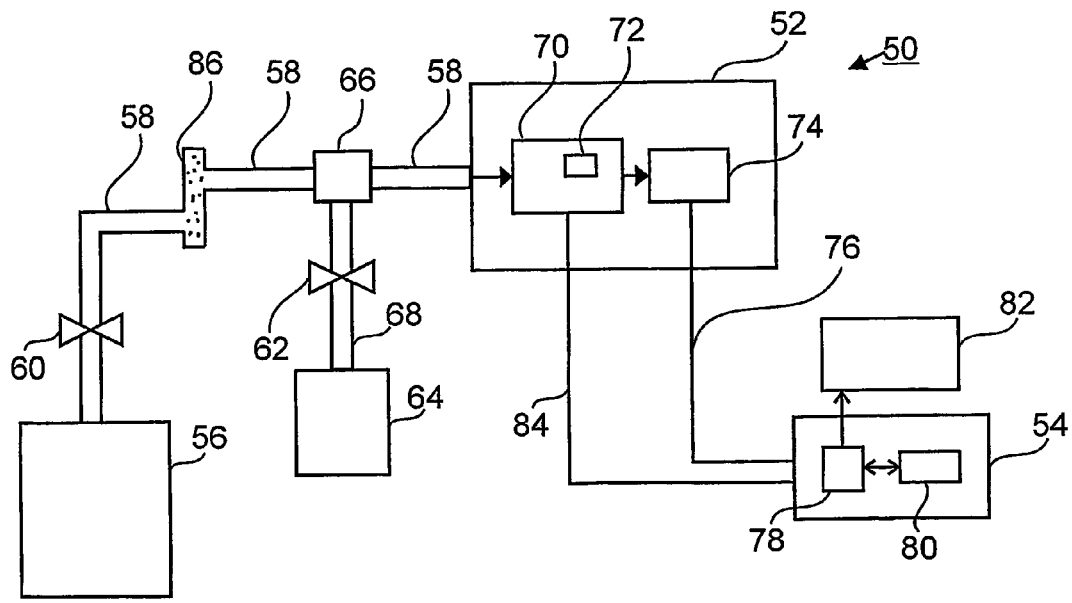
FIG. 2 is a simplified block diagram of a FAIMS apparatus according to a first embodiment of the instant invention.

Referring now to FIG. 2, shown is a FAIMS apparatus according to a first embodiment of the instant invention. The apparatus, shown generally at 50, includes an analyzer portion 52, a control portion 54, a first gas source portion 56, a second gas source portion 64 and a gas-mixing portion 66. The first gas source portion 56 is in fluid communication with the analyzer portion via a gas transfer line 58. A first flow controller or valve 60 is disposed at a point along the length of the gas transfer line 58 for adjusting a flow rate of a first gas from the first gas source portion 56. A second flow controller or valve 62 is disposed at a point along the length of a second gas transfer line 68 that is intermediate the second gas source portion 64 and the mixing portion 66. The second flow controller or valve 62 is for adjusting a flow rate of a second gas from a second gas source portion 64. The analyzer portion 52 includes a high field asymmetric waveform ion mobility spectrometer (FAIMS) 70. For instance, the FAIMS 70 is in the form of one of a cylindrical geometry domed-FAIMS, a side-to-side FAIMS and a parallel plate FAIMS. An ionization source 72 is provided in communication with the FAIMS 70 for providing sample ions thereto. During use, the ions of interest are transmitted through the FAIMS 70 and detected. For instance, the ions of interest are extracted from the FAIMS 70 for introduction into a mass spectrometer 74. The mass spectrometer 74 provides an electrical signal, which is proportional to a measured ion current of the transmitted ions, to the control portion 54 via a first communication line 76. For instance, the control portion 54 is a micro-computer including a processor 78 and a memory 80. The control portion 54 is in electrical communication with a display device 82, for providing information to a user of the apparatus 50. The control portion 54 is also in electrical communication with the FAIMS 70 via a second communication line 84 for controlling the application of an asymmetric waveform voltage and a direct current compensation voltage to not illustrated electrodes of the FAIMS 70.

Referring still to FIG. 2, the apparatus 50 further includes a gas filter, for instance a charcoal/molecular sieve filter 86, which is disposed at a point along the gas transfer line 58 intermediate the first gas source portion 56 and the mixing chamber 66. The purpose of the gas filter is to remove traces of water and/or other contaminants from the first gas provided from the first gas source portion 56. This is particularly important when a gas that is being used as a dopant gas is also present in unknown trace amounts in the first gas. For instance, the trace amounts of water and/or other contaminants originating from the first gas source portion 56 may be large relative to a desired final concentration of the dopant gas in the final carrier gas stream. Optionally, a not illustrated second gas filter is disposed at a point along the second gas transfer line 68 for removing traces of water and/or other contaminants from the second gas provided from the second gas source portion 64. Of course, the second gas filter must not remove the dopant gas contained within the second gas.

During use, the first gas is mixed with and dilutes the second gas within the gas-mixing portion 66. Preferably, the first gas comprises a purified carrier gas such as for instance one of purified oxygen, purified nitrogen and purified air. The second gas preferably comprises a same purified carrier gas mixed with a known amount of a dopant gas. Alternatively, the second gas comprises a different purified carrier gas mixed with a known amount of a dopant gas. Preferably, the dopant gas is present in the second gas in an amount that is less than approximately two percent by volume. Most preferably, the dopant gas is present in the second gas in an amount that is less than approximately 5000 ppm. In particular, the dopant gas is provided in the second gas in an amount that, when diluted by the first gas, produces a final dopant gas concentration of less than approximately one percent by volume.

The dopant gas is selected based upon a type of ion that is to be separated. Since the effect of a particular dopant gas on a given type of ion is difficult to predict, the selection of said dopant gas generally involves experimentation that is well within the ability of one of skill in the art. Preferably, a plurality of dopant gases is identified as being likely suitable for use with the given type of ions, prior to performing the experimental evaluation of the effectiveness of each one of the plurality of likely suitable dopant gases. For example, such identification may be performed by taking into account previous observations relating to similar types of ions. Ultimately, trial and error type experiments may be performed in order to identify the particular dopant gas that yields improved results for the given type of ion. Similarly, experimentation is required to determine an optimal amount of the dopant gas within the carrier gas stream for improving at least one of the sensitivity and ion separation capabilities of the FAIMS toward the given type of ion. Of course, the steps for selecting the dopant gas and for determining the optimal amount of the dopant gas within the carrier gas stream need to be performed once only. Preferably, a library including a plurality of predetermined methods is available, each method including an identity and an optimal amount of a dopant gas for analyzing a particular type of ion.

Figure 3:
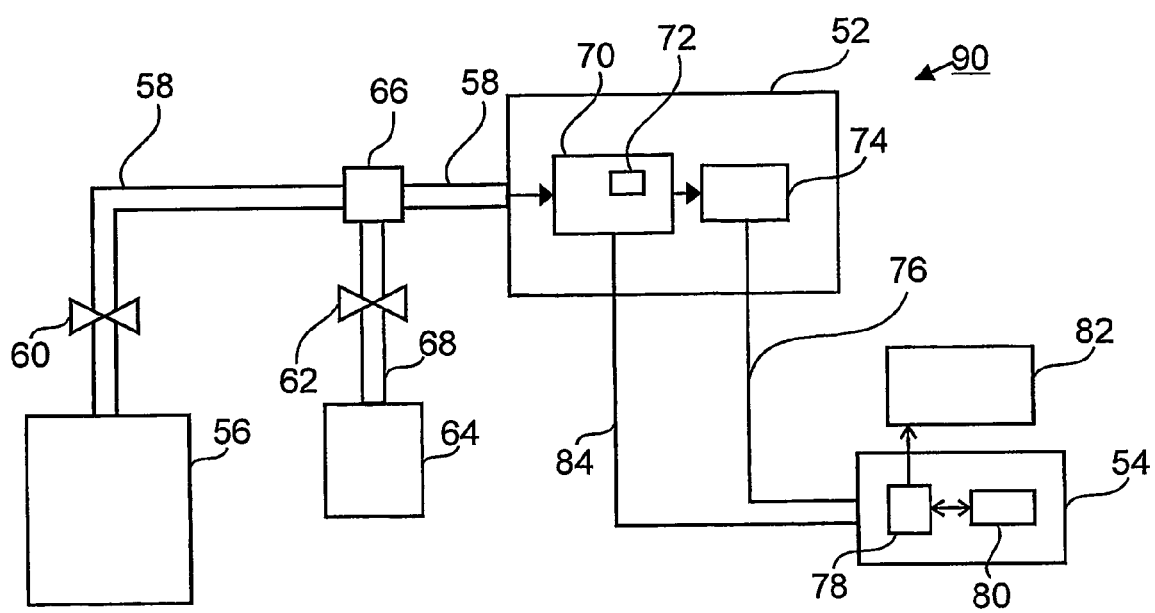
FIG. 3 is a simplified block diagram of a FAIMS apparatus according to a second embodiment of the instant invention.

Referring now to FIG. 3, shown is a FAIMS apparatus according to a second embodiment of the instant invention.

Elements labeled with the same numerals have the same function as those illustrated in FIG. 2. The apparatus, shown generally at 90 does not include a gas filter at a point along the gas transfer line 58. Accordingly, the first gas is preferably absent traces of water and/or other contaminants that adversely affect the sensitivity and/or separation capability of the FAIMS 50 toward the given type of ion.

Figure 4A:
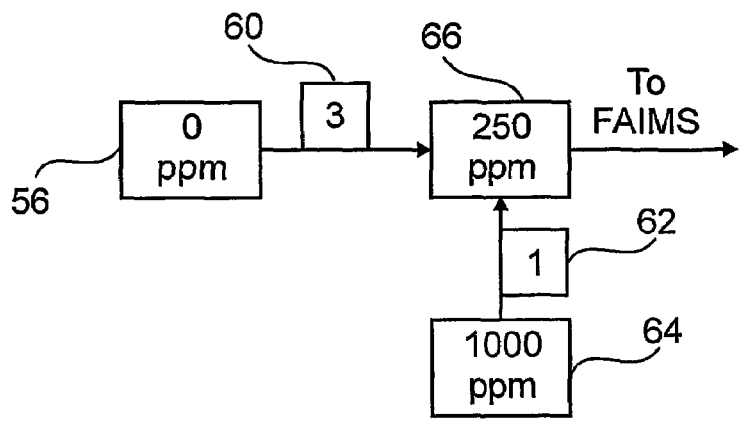
FIG. 4a shows a schematic block diagram of the gas supply and gas mixing portions of the apparatus described with reference to FIG. 2, providing a 3:1 purified carrier gas to doped carrier gas ratio.
Figure 4B:
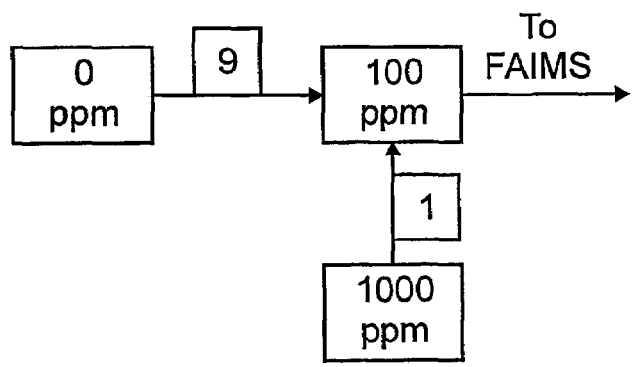
FIG. 4b shows a schematic block diagram of the gas supply and gas mixing portions of the apparatus described with reference to FIG. 2, providing a 9:1 purified carrier gas to doped carrier gas ratio.
Figure 4C:
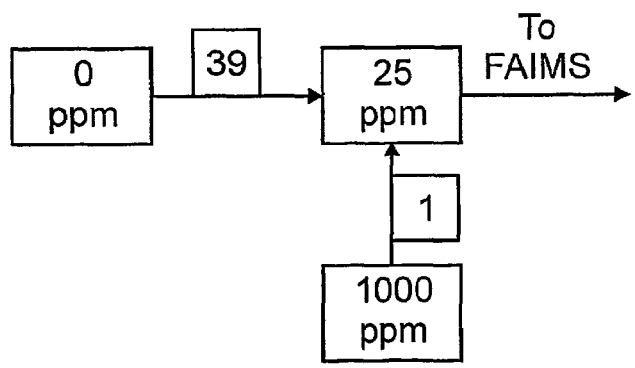
FIG. 4c shows a schematic block diagram of the gas supply and gas mixing portions of the apparatus described with reference to FIG. 2, providing a 39:1 purified carrier gas to doped carrier gas ratio.
Figure 4D:
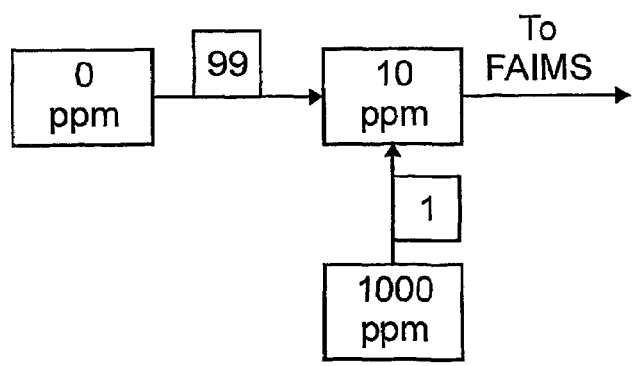
FIG. 4d shows a schematic block diagram of the gas supply and gas mixing portions of the apparatus described with reference to FIG. 2, providing a 99:1 purified carrier gas to doped carrier gas ratio.

Referring now to FIG. 4a, shown is a schematic block diagram of the gas supply and gas mixing portions of the apparatus 50 described with reference to FIG. 2. Elements labeled with the same numerals have the same function as those illustrated in FIG. 2. In the instant example, the first gas includes 0 ppm of the dopant gas, and the second gas includes 1000 ppm of the dopant gas. In order to provide a carrier gas flow to the FAIMS 70 that includes, for instance, 250 ppm of the dopant gas, the ratio of a flow rate of the first gas through the first flow controller 60 to a flow rate of the second gas through the second flow controller 62 is set to 3:1, as indicated by the numerals that are bounded by the flow controllers 60 and 62, respectively. Referring now to FIGS. 4b, 4c and 4d, the ratios of flow rates that are required to achieve a dopant gas concentration of 100 ppm, 25 ppm and 10 ppm in the carrier gas flow are 9:1, 39:1 and 99:1, respectively. Accordingly, high quality flow controllers are required to provide an accurately known amount of the dopant gas in the carrier gas stream over a wide range of dopant gas concentration values, such as for example 10 ppm to 1000 ppm. Alternatively, when dopant gas concentrations approaching the lower limit of the range are desired, the second gas source portion is replaced with a source of a second gas containing a lower concentration of the dopant gas, such that smaller ratios of flow rates are used to achieve the desired dopant gas concentration.

Figure 5:
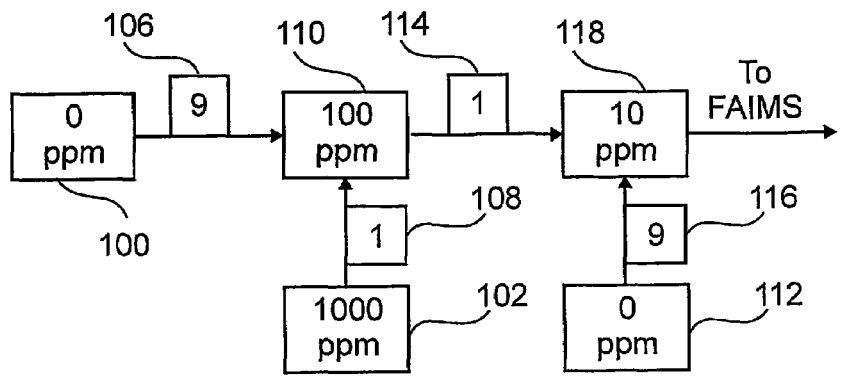
FIG. 5 is an alternative arrangement of the gas supply and gas mixing portions that is suitable for providing a desired amount of a dopant gas in a carrier gas stream of a FAIMS analyzer.

Referring now to FIG. 5, shown is an alternative arrangement of the gas supply and gas mixing portions that is suitable for providing a desired final concentration of the dopant gas in the carrier gas stream of a FAIMS analyzer. According to the alternative arrangement, a purified carrier gas absent the dopant gas is provided at first gas source 100 and a second gas containing for example 1000 ppm of the dopant gas is provided at second gas source 102. A first flow controller 106 is provided for controllably varying a flow rate of the purified carrier gas from the first gas source 100 to a mixing chamber 110, and a second flow controller 108 is provided for controllably varying a flow rate of the second gas from the second gas source 102 to the mixing chamber 110. The purified carrier gas and the second gas are mixed within the mixing chamber 110, to produce a gas mixture including a trace amount of the dopant gas. Furthermore, a third flow controller 114 is provided for controllably varying a flow rate of the gas mixture from the mixing chamber 110 to a second mixing chamber 118. A fourth flow controller 116 is provided for controllably varying a flow rate of a purified carrier gas from a third gas source 112 to the second mixing chamber 118, where it is mixed with the mixed gas to produce a carrier gas having a final dopant gas concentration. The carrier gas having a final dopant gas concentration is provided from the second mixing chamber 118 to the FAIMS.

In the example that is shown in FIG. 5, the mixing ratio of purified carrier gas to the second gas is 9:1, resulting in a 10-fold dilution of the second gas. Purified carrier gas from the third gas source 112 is used to achieve a second 10-fold dilution of the mixed carrier gas to a final concentration of 10 ppm. Step-wise dilution of a doped gas is advantageous for several reasons. First, the second gas may be prepared with an initial dopant gas concentration that is relatively large, such as for example 1000 ppm. Accordingly, a wide range of final dopant gas concentrations is accessible by varying the flow rates of purified carrier gas and of the second gas, and by varying the number of dilutions that is performed. For instance, omitting the second dilution step results in a final carrier gas concentration of 100 ppm instead of 10 ppm. Secondly, performing two or more dilutions in series allows smaller mixing ratios to be used during each dilution step, resulting in smaller errors associated with flow rate control. Advantageously, the reproducibility of the final dopant gas concentration is improved, and the comparison of experimental data to calibration data obtained at a known dopant gas concentration is more accurate. Optionally, the purified carrier gases from the first and third gas sources 100 and 112, respectively, are different purified carrier gases.

Figure 6A:
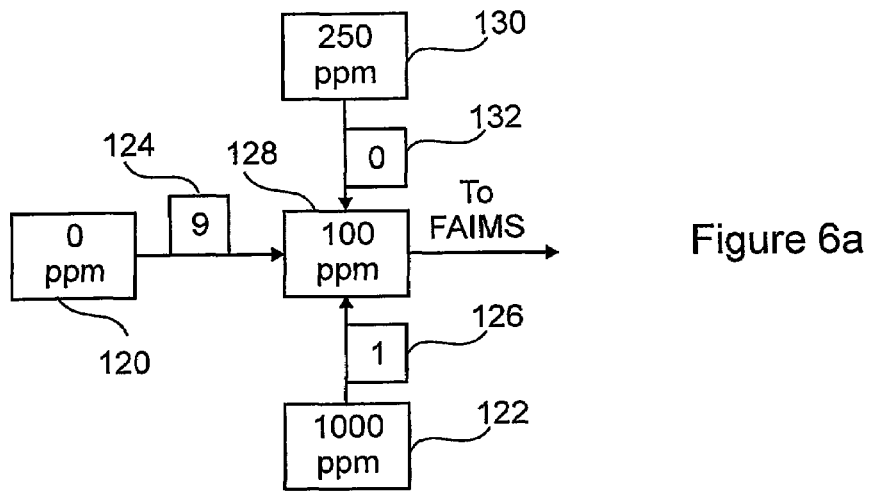
FIG. 6a is a second alternative arrangement of the gas supply and gas mixing portions that is suitable for providing a desired amount of a dopant gas in a carrier gas stream of a FAIMS analyzer, in a first mode of operation.
Figure 6B:
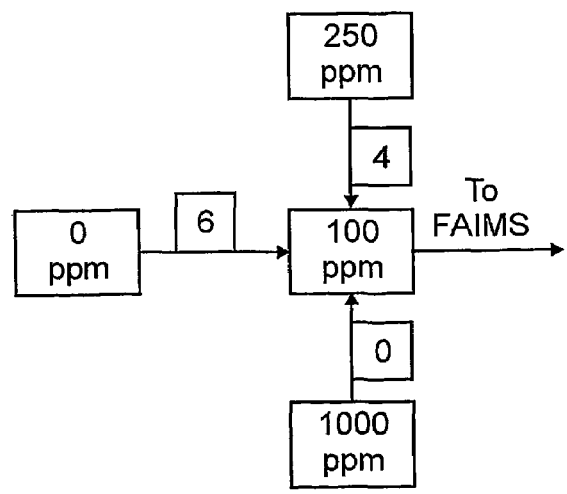
FIG. 6b shows the arrangement of FIG. 6a in a second mode of operation.

Referring now to FIGS. 6a and 6b, shown is a second alternative arrangement of the gas supply and gas mixing portions that is suitable for providing a desired amount of the dopant gas in the carrier gas stream of a FAIMS analyzer. According to the second alternative arrangement, two separate sources of doped carrier gas are provided. In particular, a first doped carrier gas source 122 containing a relatively high concentration of dopant gas and a second doped carrier gas source 130 containing a relatively low concentration of dopant gas are provided in fluid communication with a mixing chamber 128. For example, the first doped carrier gas source 122 contains 1000 ppm of the dopant gas and the second doped carrier gas source 130 contains 250 ppm of the dopant gas. A source of purified carrier gas 120 is also provided in fluid communication with the mixing chamber 128. Referring now to FIG. 6a, a final dopant gas concentration of 100 ppm is obtained by providing to the mixing chamber 128 a flow of the purified carrier gas through a first flow controller 124 that is nine times larger than a flow of the first doped carrier gas through a second flow controller 126. Referring now to FIG. 6b, the same final dopant gas concentration of 100 ppm is obtained by providing a 6:4 ratio of the purified carrier gas and the second doped carrier gas to the mixing chamber 128. Accordingly, the flow rates through the first flow controller 124 and a second flow controller 132 are similar, which reduces errors that are associated with operating one flow controller at a significantly lower flow rate compared to a second flow controller. The alternative arrangement of the gas supply and gas mixing portions described with reference to FIGS. 6a and 6b support a wide range of final dopant gas concentrations. Optionally, the second doped carrier gas source 130 is replaced with a not illustrated second source of a purified carrier gas, for diluting the gas mixture produced within the mixing chamber 128.

Further optionally, the first and second doped carrier gas sources 122 and 130, respectively, are in fluid communication with a not illustrated gas manifold, which is for receiving a flow of at least one of the first and second doped carrier gases. The not illustrated gas manifold is also in fluid communication with the mixing chamber 128 for providing the received flow of at least one of the first and second doped carrier gases thereto. The gas manifold functions as a flow selector for selectively switching between a flow of the first doped carrier gas and a flow of the second doped carrier gas. Optionally, the gas manifold can also function as a flow combiner for providing a combined flow of gas including the first doped carrier gas and the second doped carrier gas, to the mixing chamber 128.

Figure 7:
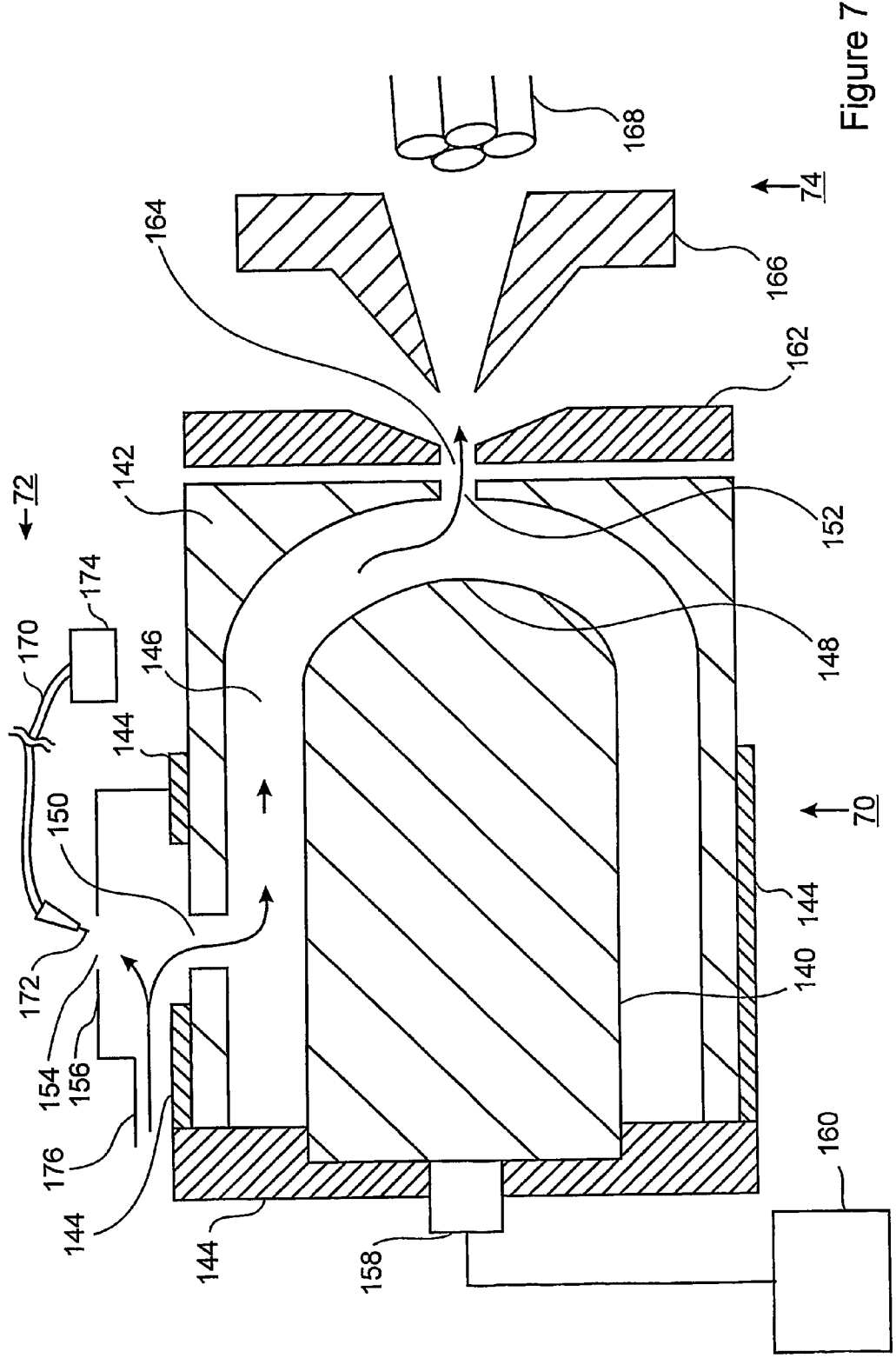
FIG. 7 shows a simplified block diagram of a domed-FAIMS analyzer for use with the apparatus of either one of FIG. 2 and FIG. 3.

Referring now to FIG. 7, shown is a specific and non-limiting example of an analyzer portion 52 that is suitable for use with the apparatus 50 and 90 that are described with reference to FIGS. 2 and 3, respectively. In particular, the FAIMS 70 is provided in the form of a cylindrical domed-FAIMS. FIG. 7 also shows an ionization source 72 and a detection system 74 in the form of an electrospray ionization source and a mass spectrometric detector, respectively. It should be clearly understood, however, that any one of a plurality of other FAIMS electrode geometries might be provided in place of the cylindrical domed-FAIMS electrode geometry that is described with reference to FIG. 7. For instance, one of a parallel plate geometry and a side-to-side geometry FAIMS is provided as the FAIMS 70. Similarly, at least one of the electrospray ionization source and the mass spectrometric detector might be replaced by another suitable ionization source and another suitable detection system, respectively.

Referring still to FIG. 7, the domed-FAIMS includes inner and outer cylindrical electrodes 140 and 142, respectively, supported by an electrically insulating material 144 in an overlapping, spaced-apart arrangement. The generally annular space between the inner electrode 140 and the outer electrode 142 defines a FAIMS analyzer region 146. The width of the analyzer region is approximately uniform around the circumference of the inner electrode 140, and extends around a curved surface terminus 148 of the inner electrode 140. Inner electrode 140 is provided with an electrical contact 158 through the insulating material 144 for connection to a power supply 160 of the FAIMS 70, that during use is capable of applying a high voltage asymmetric waveform voltage (DV) and a low voltage dc compensation voltage (CV) to the inner FAIMS electrode 140. A particular type of ion is transmitted through the analyzer region 146 at a given combination of CV and DV, on the basis of the high field mobility properties of the ion.

An ion inlet orifice 150 is provided through the outer electrode 142 for introducing ions produced at the ionization source 72 into the analyzer region 146. For example, the ionization source 72 is in the form of an electrospray ionization ion source including a liquid delivery capillary 170, a fine-tipped electrospray needle 172 that is held at high voltage (power supply not shown) and a curtain plate 156 serving as a counter-electrode for electrospray needle 172. The liquid delivery capillary 170 is in fluid communication with sample reservoir 174 containing a solution of an ion precursor. Ions are produced by the very strong electric field at the electrospray needle 172 from the solution of an ion precursor. The potential gradient accelerates the ions away from the electrospray needle 172, towards the curtain plate electrode 156. A portion of the ions pass through an orifice 154 in the curtain plate electrode 156, become entrained in a flow of a carrier gas, which is represented in FIG. 7 by a series of closed-headed arrows, and are carried into the FAIMS analyzer region 146. The flow of a carrier gas is provided through the analyzer region 146 to carry the ions toward an ion outlet orifice 152 located opposite the curved surface terminus 148 of the inner electrode 140. The orifice 154 within the curtain plate electrode 156 allows for the flow of a portion of the carrier gas in a direction that is counter-current to the direction in which the ions are traveling near the ion inlet 150, so as to desolvate the ions before they are introduced into the analyzer region 146. Once inside the FAIMS analyzer region 146, the ions are transmitted through an electric field that is formed within the FAIMS analyzer region 146 by the application of the DV and the CV to the inner FAIMS electrode 140 via the electrical contact 158.

Since the electric field also extends around the curved surface terminus 148, the transmitted ions tend to be directed generally radially inwardly towards the ion outlet orifice 152.

Referring still to FIG. 7, a mass spectrometer detector 74 is disposed external to the FAIMS analyzer region 146, and includes an orifice plate 162 having an inlet orifice 164 extending therethrough. As will be apparent to one of skill in the art, the size of the inlet orifice 164 is typically very small, being limited by the pumping efficiency of a not illustrated mass spectrometer vacuum system. The inlet orifice 164 in the orifice plate 162 is aligned with the ion outlet orifice 152 of the domed-FAIMS apparatus such that ions being extracted through the ion outlet orifice 152 enter the mass spectrometer inlet orifice 164. Those ions that pass through the orifice 164 in the orifice plate 162 travel to a skimmer cone 166 within the differentially pumped region of the mass spectrometer, and are analyzed within a mass analyzer 168 on the basis of their mass-to-charge ratio. The mass spectrometer includes a not illustrated detector, such as for instance an electron multiplier, for providing an electrical signal that is proportional to a detected ion current.

Particular features of the invention will now be illustrated with reference to two specific and non-limiting examples. In the first example, trace amounts of 2-chlorobutane in a carrier gas stream are used to improve the separation capability of the +5 charge state of bovine insulin and the +6 charge state of bovine insulin. An apparatus similar to the one that is shown at FIG. 2 was used to obtain compensation voltage spectra (CV spectra) for the +5 and +6 charge states of bovine insulin. The analyzer portion of the apparatus included the elements that were described with reference to FIG. 7. In addition, a charcoal/molecular sieve filter was disposed at a point along the second gas transfer line 68 for removing traces of water and other contaminants from the second gas before mixing with a purified carrier gas. In the second example, trace amounts of water vapour in a carrier gas stream are used to improve the signal intensity of amphetamine and a series of related compounds.

EXAMPLE 1

Bovine insulin, having a molecular weight of 5735 Da, was obtained in powdered form. A stock solution containing bovine insulin was prepared by dissolving a known amount of the bovine insulin powder in a solvent containing 1% ACS grade glacial acetic acid (acetic acid) in distilled/deionized water (DDW). Running solutions containing bovine insulin were prepared by adding known amounts of the stock solution, DDW, HPLC grade methanol (methanol), and acetic acid so that the concentration of the bovine insulin was approximately 2 µM and the solvent included a mixture of approximately 49.5% by volume DDW, 49.5% by volume methanol, and 1% by volume acetic acid. For example, to prepare 2 mL of a running solution, the following solutions were transferred to a glass vial using eppendorf pipets: 990 µL of methanol, 970 µL of DDW, 20 µL of a 200 µM stock solution, and 20 µL of acetic acid. The glass vial was sealed with a screw top cap and shaken to ensure homogeneity of the solution.

A 250 µL syringe was rinsed at least three times with a solution blank, such as for example a solution without bovine insulin present and including approximately 1% by volume acetic acid in a mixture of 1:1 DDW/methanol by volume. The 250 µL syringe was rinsed at least three times with the running solution before filling the 250 µL syringe with the running solution for analysis. The 250 µL syringe served as the sample reservoir 174 of FIG. 7, which was in fluid communication with the electrospray needle 172 via the liquid delivery capillary 170 for transferring the running solution from the 250 µL syringe to the electrospray needle 172. The electrospray needle 172 was prepared using a new piece of fused silica capillary of approximately 50 cm in length and having a 50 µm inner diameter and a 180 µm outer diameter, which was fit into a 10-cm long stainless steel capillary having a 200 µm inner diameter and 430 µm outer diameter, and allowed to protrude about 1 mm beyond the end of the stainless steel. This stainless steel capillary, in turn, protruded about 5 mm beyond the end of a larger stainless steel capillary of 15 cm in length with a 500 µm inner diameter and a 1.6 mm outer diameter, that was used for structural support and application of the high voltage necessary for electrospray. A Harvard® Apparatus Model 22 syringe pump (not shown) was used to deliver the solution from the 250 µL syringe to the end of the fused silica capillary at a flow rate of 1 µL/min. Prior to analyzing the running solution, the ionization source 72 was flushed with a solution blank at a flow rate of 1 µL/min for 10 minutes.

The tip of the electrospray needle 172 was placed approximately 1 cm away from, and slightly off-centre at an angle of approximately 45 degrees to, the curtain plate electrode 156 of the electrospray ionization source 72 of FIG. 7. Such an orientation of the electrospray needle 172 avoids the transfer of large droplets into the FAIMS analyzer region 146. The electrospray needle 172 was held at approximately 4000 V generating a current of about 180 nA for the running solution. To optimize the electrospray process, the distance that the fused silica capillary protruded from the 10 cm long stainless steel capillary was adjusted until the current was stable at a value near 180 nA. The voltage applied to the curtain plate electrode 156 was 1000 V and the curtain plate electrode 156 was isolated from the FAIMS outer electrode 142. The outer electrode 142 made electrical contact with the orifice plate 162 of the mass spectrometer, which were both held at +20 V. The FAIMS 70 was operated in P2 mode; that is to say the asymmetric waveform has a negative DV value. The width of the FAIMS analyzer region 146 was approximately 1.5 mm, and the width of an extraction region intermediate the curved surface terminus 148 of the inner electrode 140 and the ion outlet orifice 152 was approximately 1.7 mm.

To generate the asymmetric waveform for the analyses described herein, a tuned electronic circuit was used that provided an appropriate combination of a sinusoidal wave and its harmonic. These waveforms are mathematically described by the equation, $$V_\alpha(t)=C+fD\sin(\omega t)+(1-f)D\sin(2\omega t-\phi) \quad (1)$$

where $V_\alpha(t)$ represents the voltage of the waveform relative to the voltage applied to the outer electrode 142 at a given time, t, C is the compensation voltage, CV, which is changed stepwise from 4.36 to −17.24 V during the acquisition of the spectra as is described below, D is the maximum voltage of the waveform or the dispersion voltage, DV=−3800 V, f is approximately 0.65, ω is the frequency (750 kHz), and ϕ is 90°.

Referring again to FIG. 2, industrial grade nitrogen gas was passed through the charcoal/molecular sieve filter 86 and a gas mixture containing 1000 ppm 2-chlorobutane in nitrogen was passed through a separate molecular sieve filter (not shown) before the gases were mixed together in the mixing chamber 66 and introduced into the FAIMS 70. Referring again to FIG. 7, the flow rates of each of these gases were adjustable and the total flow rate into a gas inlet 176 of the FAIMS 70 was fixed at 1.2 L/min. Thus to obtain, for example, a mixture containing 250 ppm 2-chlorobutane in nitrogen as the doped carrier gas, the flow rate for the industrial grade nitrogen gas was set to 0.9 L/min and the flow rate for the gas mixture containing 1000 ppm 2-chlorobutane in nitrogen was set to 0.3 L/min. With the exception of 0 L/min, the flow rate of the gas mixture of 1000 ppm 2-chlorobutane in nitrogen was varied from 0.03 to 1.20 L/min giving a range of approximately 25 to 1000 ppm of 2-chlorobutane in the nitrogen carrier gas. As is shown in FIG. 7, the total gas flow splits into two portions including a first portion flowing out through the curtain plate orifice 154 in a direction that is countercurrent to the arriving electrospray ions, thereby facilitating desolvation of the electrospray ions. A second portion of the total gas flow carries the ions inward through the ion inlet orifice 150 in the outer FAIMS electrode 142 and along the analyzer region 146 of the device. Ions transmitted by the FAIMS device were detected using the API 300 triple quadrupole mass spectrometer.

Electrospray ionization of bovine insulin produces a distribution of ions of the form $[M+zH]^{z+}$, where M is the molecular weight of bovine insulin protein (5735 Da), z is a number (e.g., 5,6,7), and H is a proton attached to the bovine insulin protein. The value of z in this example can also be used to refer to the charge state of the ion. For analyzing electrospray generated ions from the running solution containing bovine insulin, the mass spectrometer was set to monitor the intensity of detected ions of the m/z value of a particular charge state so as to produce an CV spectrum. For example, when analyzing a running solution, the CV was scanned from 4.36 to −17.24 V in 240 incremental steps each of approximately −0.09 V. In one CV scan, charge state (z)+5 was monitored, which means that an m/z value of 1148.0 was monitored. When the CV scan was initiated, the CV value was 4.36 V and the quadrupole mass analyzer was set to selectively detect m/z 1148.0 for 1000 ms. The CV was then stepped to 4.27 V and the quadrupole mass analyzer selectively measured the ion intensity for another 1000 ms. This process of stepping the CV and selectively detecting m/z 1148.0 was repeated until a total of 241 points were obtained. From this data, a plot of the ion intensity as a function of the CV was obtained for the +5 charge state. Several of these plots were acquired with different amounts of 2-chlorobutane added to the carrier gas. CV spectra for other charge states were monitored in an analogous way using the same running solution.

FIGS. 8a to 8e show five CV spectra for the +5 charge state of bovine insulin using a carrier gas comprising nitrogen mixed with different amounts, for instance 0, 250, 500, 750, and 1000 ppm, respectively, of 2-chlorobutane vapour. The ordinate in each plot represents the signal intensity of the +5 ion measured in counts per second, and the abscissa represents the CV range between +4 to −17 V. FIG. 8a shows an CV spectrum that was recorded with no 2-chlorobutane vapour present in the purified carrier gas. FIG. 8b shows a spectrum collected in a manner identical to that in FIG. 8a, but with 250 ppm of 2-chlorobutane vapour added to the carrier gas stream. The CV spectrum shown in FIG. 8b indicates that the presence of 250 ppm of 2-chlorobutane vapour in the nitrogen gas stream results in a decrease in the ability of the FAIMS to separate the two main peaks that were observed in FIG. 8a, and in addition the CV of transmission has also become about 4 volts less negative.

Each successive trace in the figure shows spectra obtained by increasing the amount of 2-chlorobutane in 250 ppm increments up to 1000 ppm. As shown in FIG. 8c, at a level of 500 ppm of 2-chlorobutane in the carrier gas, shoulders are observed on a broad peak suggesting several closely related species that are not well separated. Further increases up to 1000 ppm, representing the maximum level that was employed in this study, continued to show improvements in the separation capabilities in the CV spectra of m/z 1148.0 and shifts in the CV of ion transmission to more positive values. As shown in FIG. 8e, at a level of 1000 ppm of 2-chlorobutane there are 5 distinct peaks that appear in the CV spectrum, each peak characterized by a mass-to-charge ratio of 1148.0. This CV spectrum shows a dramatic change compared with the CV spectrum that was obtained without 2-chlorobutane present being present in the carrier gas. Although a loss in signal intensity is observed, which is likely due to decreased ion focusing that is generally associated with lower magnitudes of CV, the addition of a trace amount of this "magic bullet" vapour has had the desired effect of enabling the separation, in terms of CV, of species that were not separated in the pure nitrogen carrier gas using the same experimental conditions. In direct contrast to previous reports, which have indicated that the separation capabilities improve as the magnitude of the CV increases, improvements in separation capabilities have unexpectedly occurred with a decrease in the magnitude of CV. This observation, which is contrary to previously published knowledge, suggests that the improvements in the separation capabilities are a result of a different mechanism than has been described previously. As a result, the behavior shown in FIGS. 8a to 8e is not predicted nor expected based upon any previous knowledge of FAIMS, including prior work which used mixed carrier gas.

Figures 9A, 9B, 9C, 9D, 9E:
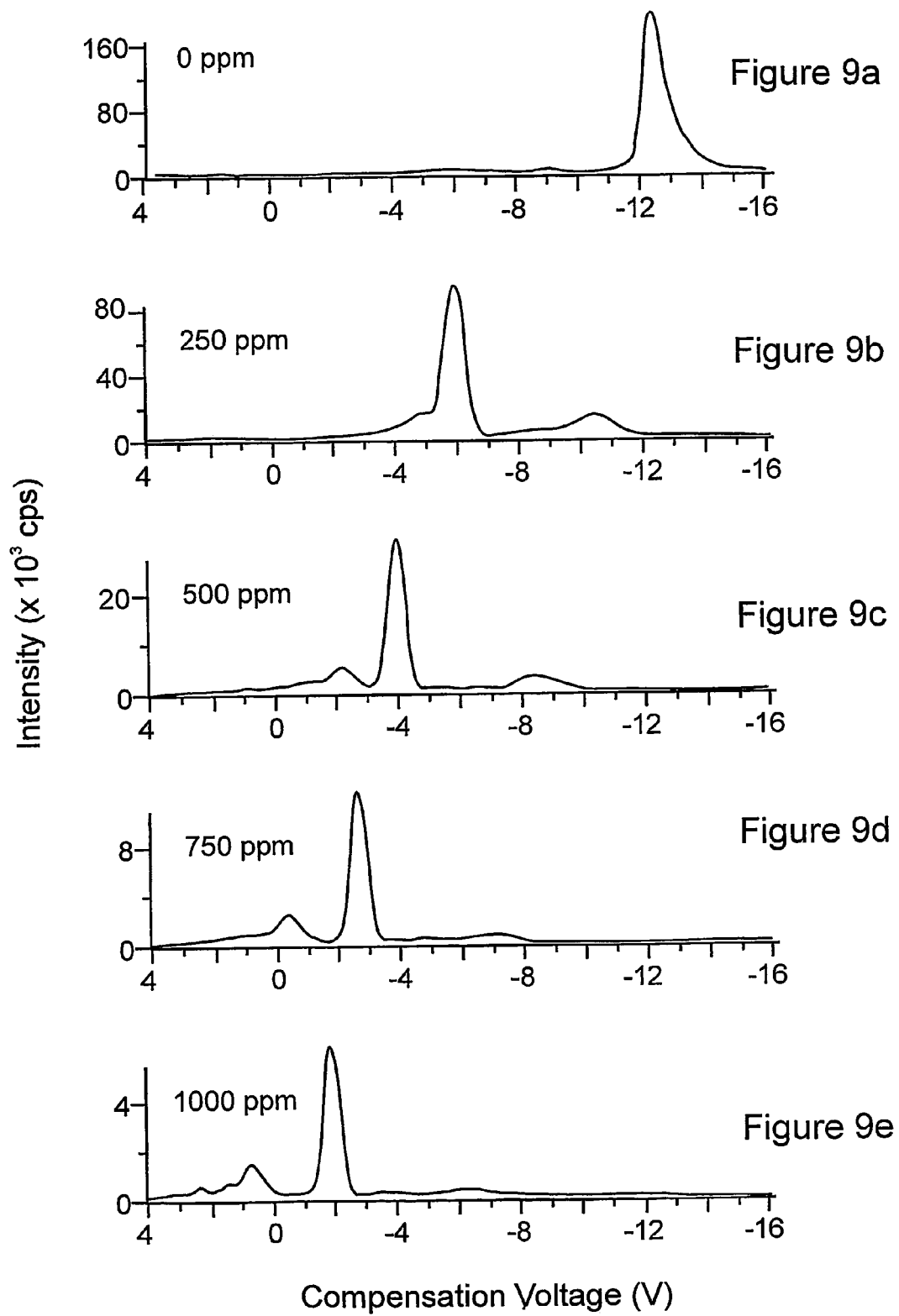
FIG. 9a shows a CV spectrum for the +6 charge state of bovine insulin when a purified carrier gas stream is used.
FIG. 9b shows a CV spectrum for the +6 charge state of bovine insulin when 250 ppm of 2-chlorobutane is added to the carrier gas stream.
FIG. 9c shows a CV spectrum for the +6 charge state of bovine insulin when 500 ppm of 2-chlorobutane is added to the carrier gas stream.
FIG. 9d shows a CV spectrum for the +6 charge state of bovine insulin when 750 ppm of 2-chlorobutane is added to the carrier gas stream.
FIG. 9e shows a CV spectrum for the +6 charge state of bovine insulin when 1000 ppm of 2-chlorobutane is added to the carrier gas stream.

The +6 charge state of bovine insulin was also experimentally investigated in a similar manner, wherein the quadrupole mass analyzer was set to selectively detect ions having an m/z value of 956.8 in order to generate the CV spectra for this charge state. FIGS. 9a to 9e show five CV spectra for the +6 charge state of bovine insulin using a carrier gas comprising purified nitrogen mixed with different amounts, for instance 0, 250, 500, 750, and 1000 ppm, respectively, of 2-chlorobutane vapour. The ordinate in each plot represents the signal intensity of the +6 ion measured in counts per second and the abscissa represents the CV range between +4 to −16 V. Referring to FIG. 9b, for the +6 charge state, there is a much more noticeable change in the CV spectrum, both in terms of the shape of the spectra and the CV values of transmission, when only 250 ppm of 2-chlorobutane was added to the carrier gas, as compared with the +5 charge state. The addition of only 250 ppm of 2-chlorobutane resulted in a shift in the CV of transmission of the most intense peak by about 6 volts more positive, with a concomitant decrease in sensitivity of about 50%. Referring now to FIG. 9c, increasing the amount of 2-chlorobutane in the carrier gas to 500 ppm resulted in additional unexpected improvements in separation. Unlike the +5 charge state that showed significant improvements up to 1000 ppm, further increases in the amount of 2-chlorobutane in excess of approximately 500 ppm resulted only in modest improvements to the separation capabilities of the +6 charge state while significantly decreasing the observed signal intensity, as shown in FIGS. 9d and 9e.

It must be emphasized that these changes in the CV of transmission of the bovine insulin ions could not be predicted from any known information about FAIMS, or known information about the ions of bovine insulin. The mechanism giving rise to the changes of the CV spectrum shown in FIGS. 8a to 8e and in FIGS. 9a to 9e are currently not well understood.

EXAMPLE 2

A fortuitous experimental observation led to the discovery that an unforeseen advantage can be obtained using water vapour as a special type of "magic bullet" vapour. This advantage corresponds to a significant improvement in the observed signal intensities for some compounds. Previous work has reported that high amounts of water vapour will cause catastrophic deterioration of CV spectra. However, the presence of water vapour at trace levels in the carrier gas stream has now been found to sometimes result in favorable changes to the CV spectra of some analytes. This unexpected behavior was observed when analyzing amphetamine and a series of related compounds. A gas purification filter (charcoal/molecular sieves) that was used for removing water vapour from a gas flow of nitrogen, which made up part of the carrier gas, was compromised by operation for a longer period of time than the filter was designed to operate. Eventually as the source nitrogen gas passed through the filter, the filter was unable to remove all of the water in the source nitrogen gas. Although the carrier gas included a mixture of helium and nitrogen, as is described below, it was only the gas purification filter that was used with the source nitrogen gas that was compromised so as to allow a small flow of water vapour, possibly at the sub-ppm level, to elute from the less than completely effective filter. Thus, some of the water vapour present in the source nitrogen gas was passed into the FAIMS device as part of the carrier gas. Although the amount of water vapour was not quantified, the level of water that was reported by the manufacturer in the source nitrogen gas was approximately 3 ppm, which was subsequently diluted by the addition of dehumidified helium.

Experimentally, the presence of water in the gas stream resulted in an increase in the CV of transmission for the electrospray generated ions of amphetamine and a series of related compounds, which more importantly, also lead to favorable changes in the signal intensity of the transmitted ions. A series of experiments were carried out on amphetamine, methamphetamine, and their methylenedioxy derivatives to illustrate the effects of water vapour on the CV spectra. Amphetamine (Am) and methamphetamine (Mam) were obtained from Alltech Associates (State College, Pa.). 3,4-Methylenedioxymethamphetamine (MDMAm), 3,4-methylenedioxyamphetamine (MDAm), were obtained from CIL Inc. (Andover, Mass.). All of these compounds were obtained as solutions, at a concentration of 1 mg/mL in methanol. A composite stock solution, 10 μg/mL of each of the four analytes, was prepared by combining aliquots of each of the commercial standards and diluting with HPLC grade methanol (methanol). A "running solution", containing approximately 50 ppb of each of the four analytes, that was used for the analysis was prepared by adding a known volume of the composite stock solution to a known volume of solvent containing approximately 0.2 mM reagent grade ammonium acetate (0.2 mM ammonium acetate) in approximately 9:1 methanol:distilled/deionized water (DDW) by volume. For example, for preparing the running solution, 10 μL of the composite stock solution and 1.99 mL were delivered to a glass vial using eppendorf pipets. The glass vial was sealed with a screw top cap and shaken to ensure homogeneity of the solution.

A 250 µL syringe was rinsed at least three times with a solution blank, such as for example a solution without the four analytes present and having approximately 0.2 mM ammonium acetate in approximately 9:1 methanol:DDW by volume. The 250 µL syringe was rinsed at least three times with the running solution before filling the 250 µL syringe with the running solution for analysis. The 250 µL syringe served as the sample reservoir 174 of FIG. 7, which was in fluid communication with the electrospray needle 172 via the liquid delivery capillary 170 for transferring the running solution from the 250 µL syringe to the electrospray needle 172. The electrospray needle 172 was prepared using a new piece of fused silica capillary of approximately 50 cm in length and having a 50 µm inner diameter and a 180 µm outer diameter, which was fit into a 10-cm long stainless steel capillary having a 200 µm inner diameter and 430 µm outer diameter, and allowed to protrude about 1 mm beyond the end of the stainless steel. This stainless steel capillary, in turn, protruded about 5 mm beyond the end of a larger stainless steel capillary of 15 cm in length with a 500 µm inner diameter and a 1.6 mm outer diameter, that was used for structural support and application of the high voltage necessary for electrospray. A Harvard® Apparatus Model 22 syringe pump (not shown) was used to deliver the solution from the 250 µL syringe to the end of the fused silica capillary at a flow rate of 1 µL/min. Prior to analyzing the running solution, the ionization source 72 was flushed with a solution blank at a flow rate of 1 µL/min for 10 minutes.

The tip of the electrospray needle 172 was placed approximately 1 cm away from, and slightly off-centre at an angle of approximately 45 degrees to, the curtain plate electrode 156 of the domed-FAIMS device of FIG. 7. Such an orientation of the electrospray needle 172 avoids the transfer of large droplets into the FAIMS analyzer region 146. The electrospray needle 172 was held at approximately 3500 V generating a current of about 45 nA while spraying the running solution. To optimize the electrospray process, the distance that the fused silica capillary protruded from the 10-cm long stainless steel capillary was adjusted until the current was stable at a value near 45 nA. The voltage on the curtain plate electrode 156 was 1000 V and the curtain plate electrode 156 was isolated from the FAIMS outer electrode 142. The outer electrode 142 made electrical contact with the orifice plate of the mass spectrometer, which were both held at +20 V. The FAIMS 70 was operated in P2 mode; that is to say the asymmetric waveform has a negative DV value. The width of the FAIMS analyzer region 146 was approximately 2 mm, and the width of an extraction region intermediate the curved surface terminus 148 of the inner electrode 140 and the ion outlet orifice 152 was approximately 1.9 mm.

To generate the asymmetric waveform for the analyses described herein, a tuned electronic circuit was used that provided an appropriate combination of a sinusoidal wave and its harmonic. These waveforms were mathematically described by equation (1). The parameters of the waveform are the same as described above, with the exception of the CV, which was scanned from +5 to −15 V.

The carrier gas comprised industrial grade nitrogen gas, which was passed through a charcoal/molecular sieve filter, and industrial grade helium gas, which was passed through a second charcoal/molecular sieve filter. Referring again to FIG. 2, these gases were mixed together in the mixing chamber 66 with the flow rate of nitrogen into the mixing chamber 66 set to 1.4 L/min and the flow of helium set to 1.4 L/min.

For the spectra that were generated using the "dry filter", the charcoal/molecular sieve filter that was used with the nitrogen source gas had been recently regenerated by heating in an oven overnight while flushing gas through to remove trapped water, and therefore this filter was operating properly. For the spectra that are generated using "wet filter", the charcoal/molecular sieve filter that was used with the nitrogen source gas was compromised. For example, the filter had not been regenerated during two months of use and therefore the molecular sieves in these filters were only able to remove a portion, or none, of the water from the nitrogen source gas. The charcoal/molecular sieve filter that was used with the helium source gas was recently regenerated and used for all the experiments.

The total gas flow splits into two portions including a first portion flowing out through the curtain plate orifice 154 in a direction that is countercurrent to the arriving electrospray ions, thereby facilitating desolvation of the electrospray ions. A second portion of the total gas flow carries the ions inward through the ion inlet orifice 150 in the outer FAIMS electrode 142 and along the analyzer region 146 of the device.

Ions transmitted by the FAIMS device were detected using an API 300 triple quadrupole mass spectrometer. Electrospray ionization of the running solution produces ions for each of these four analytes of the form $[M+H]^+$, where M is the molecular weight of the analyte and H is a proton. For analyzing electrospray generated ions of the four analytes, the m/z values of the $[M+H]^+$ ion for each analyte was monitored as the CV was scanned. That is, when analyzing the running solution, the CV was scanned from 5.0 to −15.0 V in 200 incremental steps of approximately −0.1 V each, while the following m/z values were monitored: 136.2 (Am), 150.2 (µm), 180.2 (MDAm), 194.2 (MD-MAm). For example, when the CV scan was initiated, the CV value was 5.0 V and the quadrupole mass analyzer began to selectively detect, one at a time, each of the four different m/z values listed above during a time period of 100 ms each. After each one of the four different m/z values was scanned, the CV was stepped to 4.9 V and after a 100 ms pause time, each of the four different m/z values was selectively detected, one at a time, again. This process of stepping the CV and selectively detecting each one of the four m/z values was repeated until a total of 201 points for each m/z value was obtained. From this data, a plot of the ion intensity as a function of the CV was made for the $[M+H]^+$ ion of each analyte. Two separate CV scans were carried out as described above, one with a "wet filter" and the other with a "dry filter". FIGS. 10*a* through 13*a* show the CV scans obtained for each analyte when a dry filter was used, and FIGS. 10*b* through 13*b* show the CV scans obtained for each analyte when a wet filter was used.

Figure 10A:
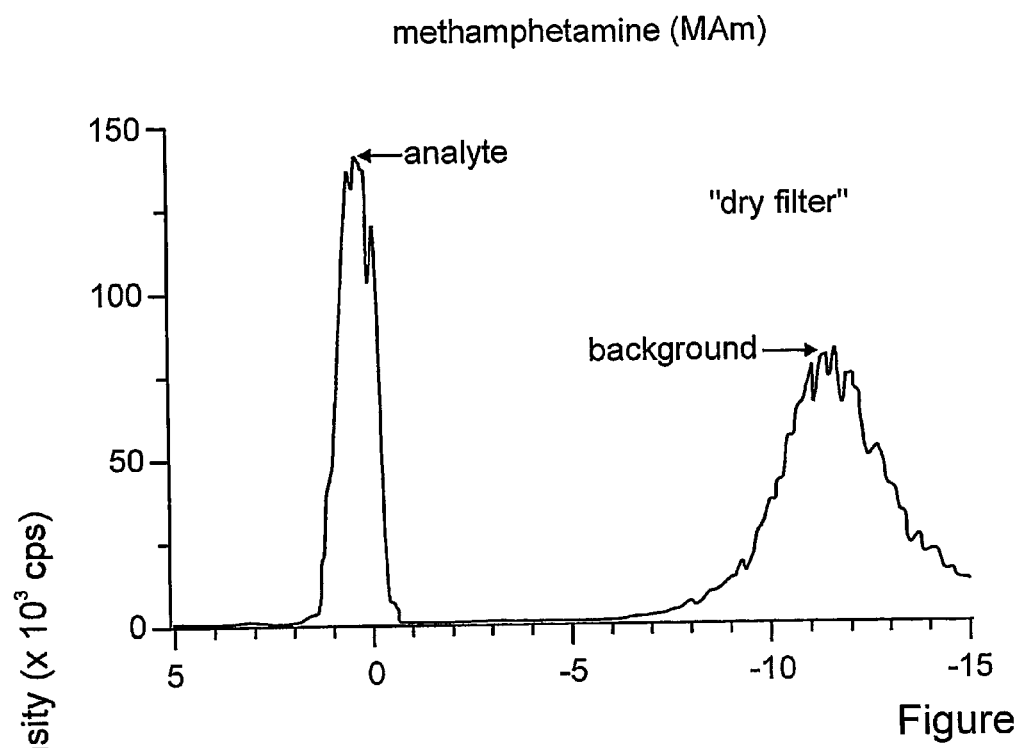
FIG. 10a shows a CV spectrum for protonated methamphetamine obtained using a dehumidified carrier gas.
Figure 10B:
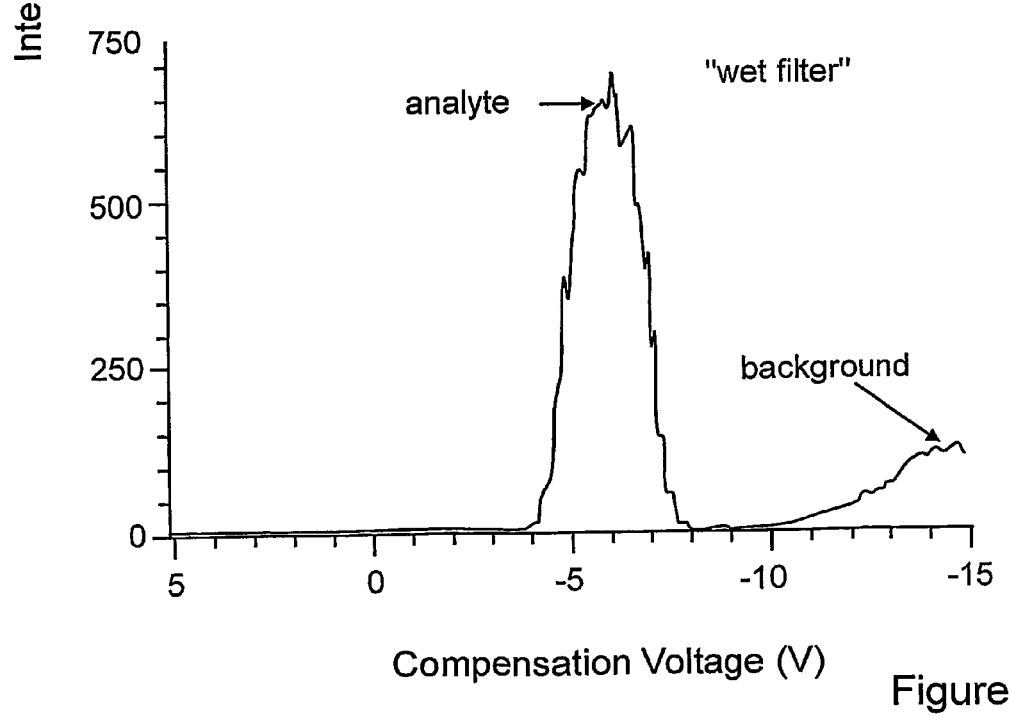
FIG. 10b shows a CV spectrum for protonated methamphetamine obtained using a carrier gas containing a trace amount of water vapour.

FIGS. 10*a* and 10*b* show the CV spectrum that was acquired for MAm using a dry filter and using a wet filter, respectively. As described above, the running solution containing the analyte was delivered by a flow of solution to an electrospray needle, continuously. The cloud of resulting ions, including the $[M+H]^+$ ion of MAm, was continuously delivered to the ion inlet of FAIMS. FIG. 10*a* shows a CV spectrum that was obtained when the gas purification filter was working properly, such that traces of water vapour were minimized in the carrier gas stream. For this analyte, the CV of optimal transmission was approximately +0.5 V and the corresponding analyte intensity at this CV was approximately 140 000 cps. When the "dry filter" was replaced with the "wet filter", which was unable to effectively remove the water present in the nitrogen gas stream, there was a shift in the optimal CV of transmission to approximately −6.0 V, as shown in FIG. 10b. Furthermore, the maximum intensity increased by approximately five-fold to 690 000 cps.

Figure 11A:
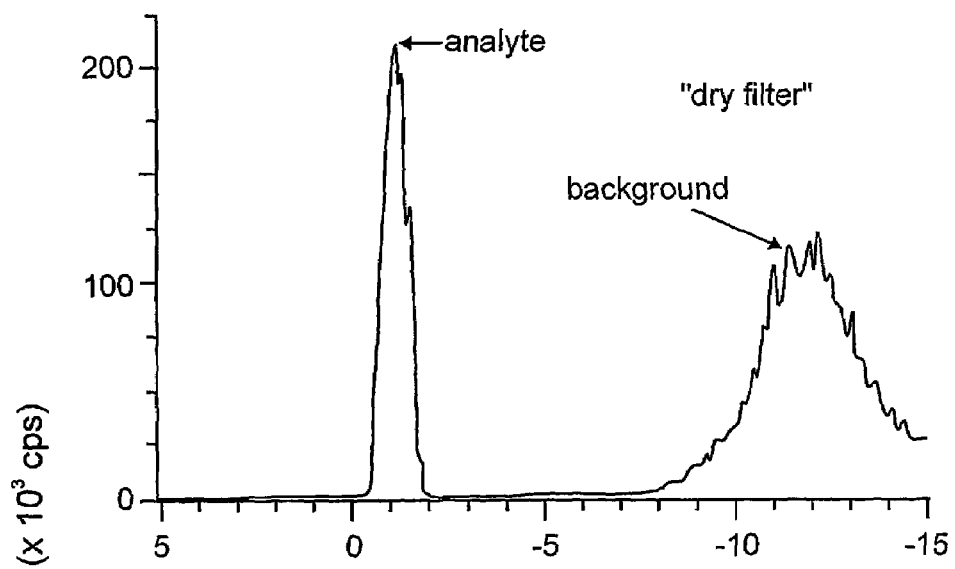
FIG. 11a shows a CV spectrum for protonated 3,4-methylenedioxymethamphetamine obtained using a dehumidified carrier gas.
Figure 11B:
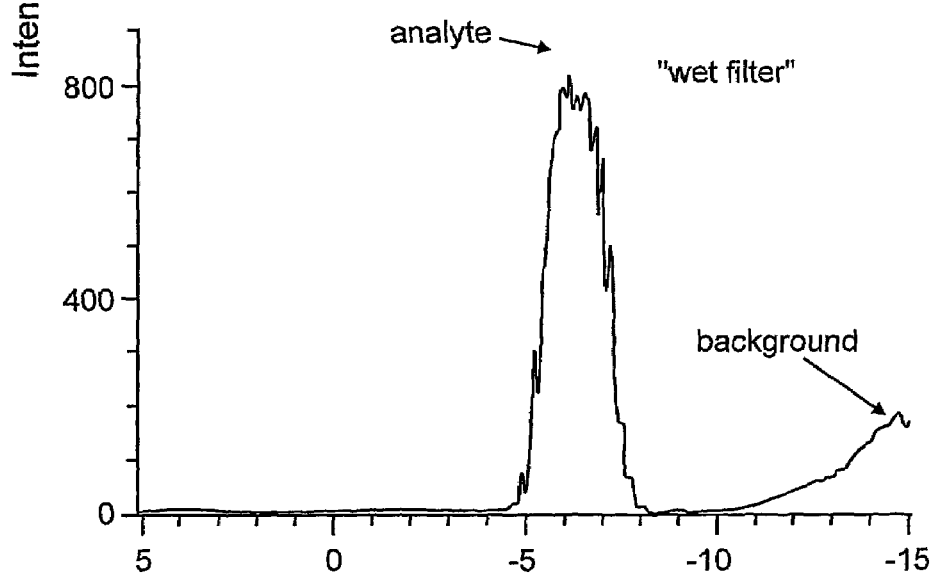
FIG. 11b shows a CV spectrum for protonated 3,4-methylenedioxymethamphetamine obtained using a carrier gas containing a trace amount of water vapour.

FIGS. 11a and 11b show the CV spectrum that was acquired for MDMAm using a dry filter and using a wet filter, respectively. Clearly, MDMAm exhibits behavior similar to that of MAm under the conditions that were used in the instant study. In particular, the presence of an approximately same amount of water in the gas stream resulted in a change in the CV of transmission from approximately −1 to −6 V and approximately a four-fold increase in the observed intensity from about 210 000 cps to about 820 000 cps.

Figure 12A:
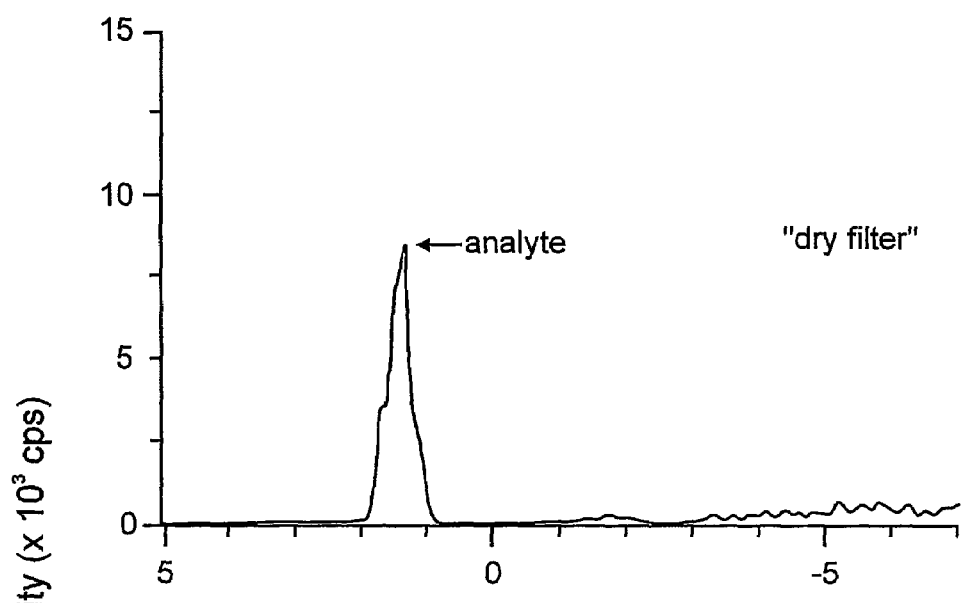
FIG. 12a shows a CV spectrum for protonated 3,4-methylenedioxyamphetamine obtained using a dehumidified carrier gas.
Figure 12B:
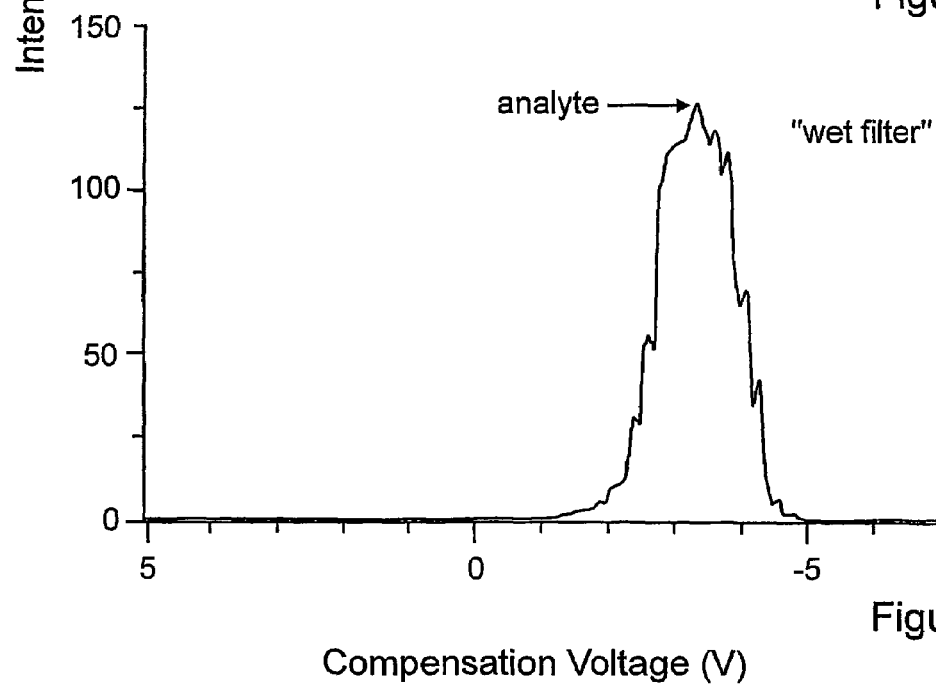
FIG. 12b shows a CV spectrum for protonated 3,4-methylenedioxyamphetamine obtained using a carrier gas containing a trace amount of water vapour.

FIGS. 12a and 12b show the CV spectrum that was acquired for MDAm using a dry filter and using a wet filter, respectively. The CV of optimal transmission for MDAm shows a shift from approximately 1.5 to approximately −3.5 V, which is accompanied by an approximate 15-fold increase in sensitivity when the "dry filter" is replaced with the "wet filter".

Figure 13A:
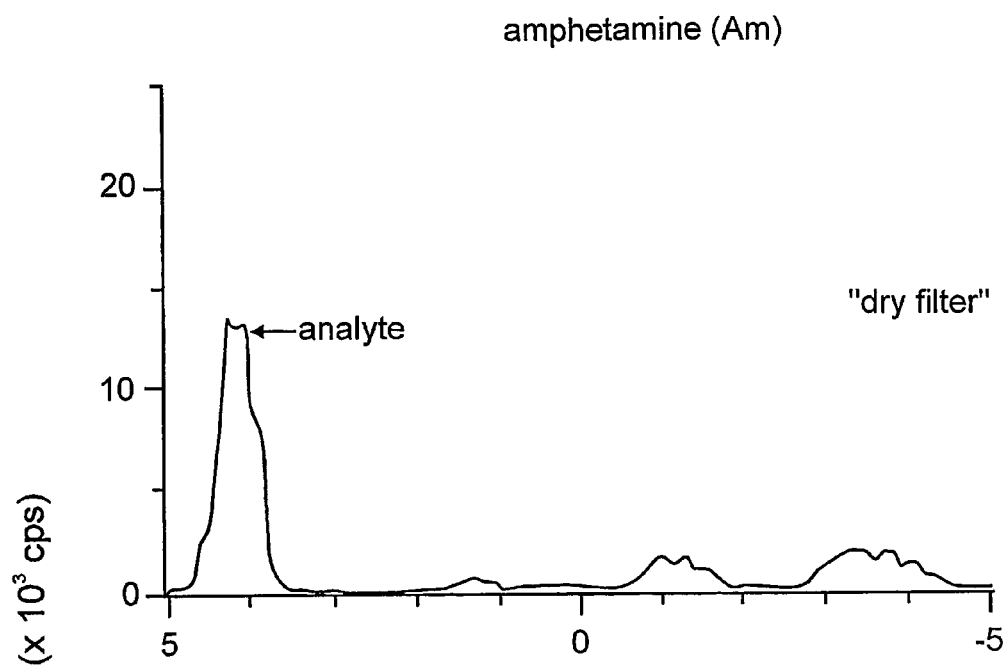
FIG. 13a shows a CV spectrum for protonated amphetamine obtained using a dehumidified carrier gas.
Figure 13B:
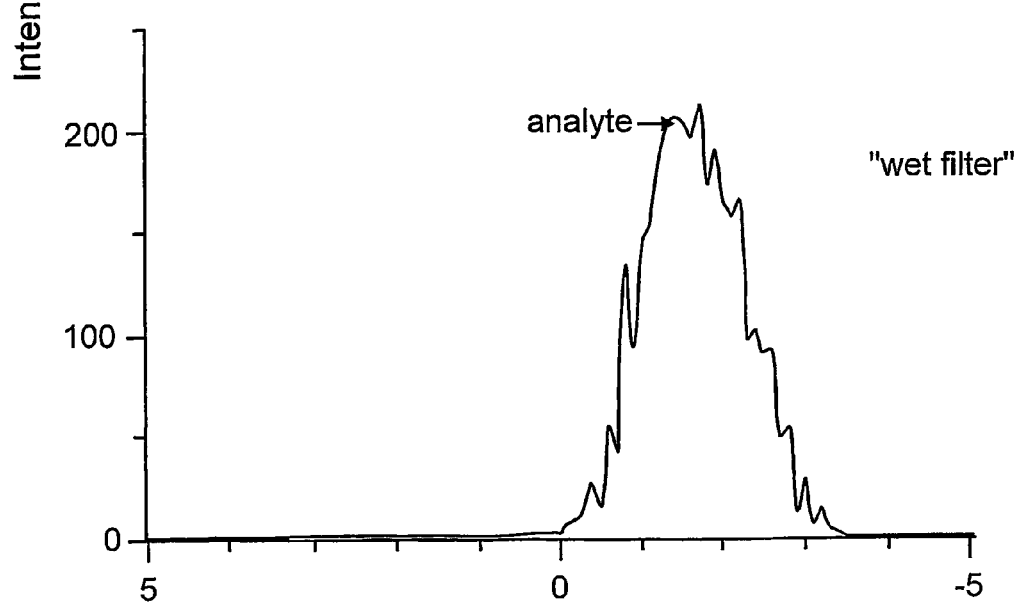
FIG. 13b shows a CV spectrum for protonated amphetamine obtained using a carrier gas containing a trace amount of water vapour.

FIGS. 13a and 13b show the CV spectrum that was acquired for Am using a dry filter and using a wet filter, respectively. The CV of optimal transmission for Am shows a shift from approximately 4 to approximately −1.5 V with an approximately 15-fold increase in sensitivity when the "dry filter" is replaced with the "wet filter".

In view of the CV spectra shown in FIGS. 10 through 13, it is apparent that the degree of benefit of having trace amounts of water vapour in the gas stream is dependent upon the type of ion being analyzed. For the investigation of the four ions shown in FIGS. 10 through 13, the most noticeable increase is observed for ions having positive or only slightly negative CV of optimal transmission, when operating using P2 mode, in the absence of traces of water in the gas stream. Advantageously, introduction of a trace amount of water into the gas stream significantly lowers the detection limits of some types of ions.

The examples of the trace vapour used to describe this present invention have shown that the interaction between an analyte and the surrounding gas is very critical. Significant changes in the CV spectra are observed when very small quantities of vapour are added to the purified carrier gas. The reason for this unexpected response is poorly understood. Some interaction is assumed to take place between the ion and the added "magic bullet" vapour, however, the nature of the interaction and its effect on ion transmission is currently unknown. This is not to say that the "magic bullet" vapours described herein will show improvements in terms of signal intensity and/or peak separation for all analytes. In fact, compounds should be anticipated to respond differently to a given "magic bullet" vapour or even a mixture of "magic bullet" vapours. In addition, depending on the desired application, it might be possible that one "magic bullet" vapour could be used to improve the peak separation capabilities, whereas a different "magic bullet" vapour could be used to improve the signal sensitivity.

Figure 14:
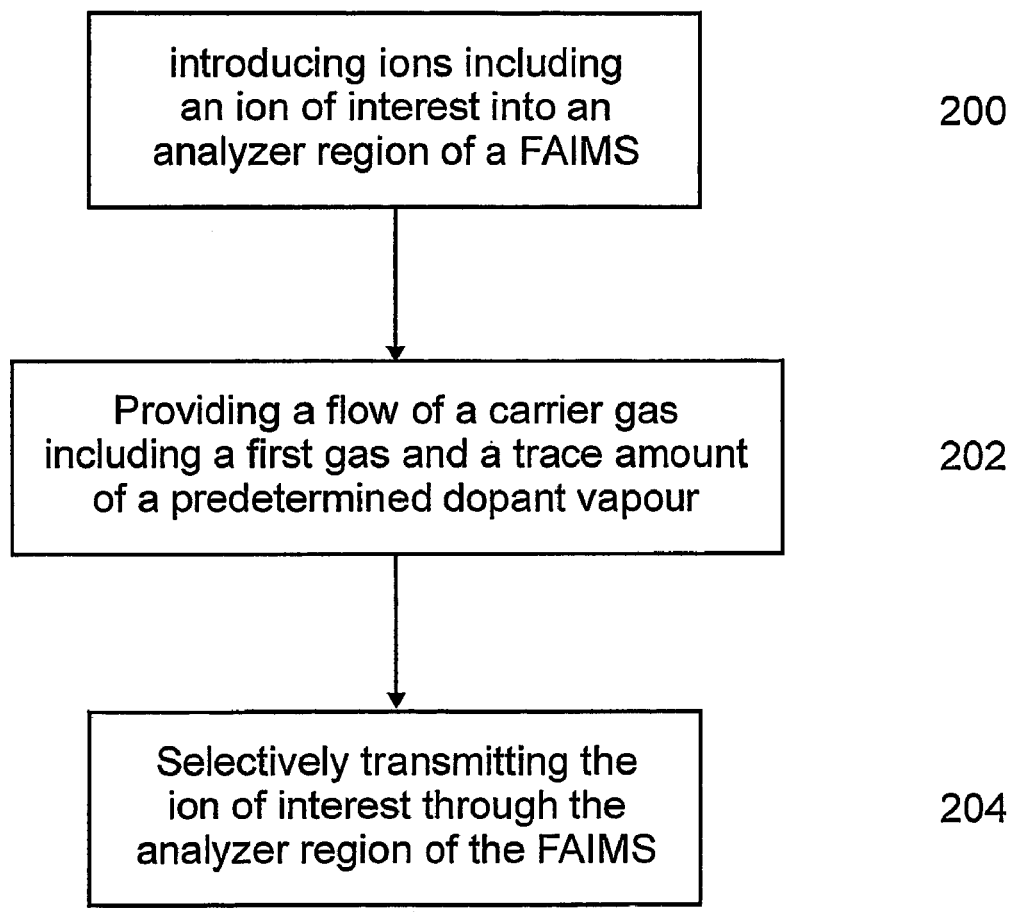
FIG. 14 is a simplified flow diagram for a method according to the instant invention of selectively transmitting ions within a FAIMS analyzer region using a carrier gas including a trace amount of an added component.

Referring now to FIG. 14, shown a simplified flow diagram for a method according to the instant invention of selectively transmitting ions within a FAIMS analyzer region using a carrier gas including a trace amount of an added component, a so called "magic bullet", such as for instance a dopant gas. At step 200, ions including an ion of interest are introduced into an analyzer region of a FAIMS. At step 202, a flow of a carrier gas is provided through the FAIMS analyzer region, the carrier gas including at least a first gas and a trace amount of a predetermined dopant gas. The predetermined dopant gas is selected for improving one of a peak separation and a signal intensity relating to the ion of interest. At step 204, the ion of interest is selectively transmitted through the FAIMS analyzer region in the presence of the carrier gas. Optionally, the method according to FIG. 14 includes a step of varying the trace amount of the predetermined dopant gas to determine an optimal trace amount of the predetermined dopant gas for improving one of the peak separation and the signal intensity relating to the ion of interest.

Figure 15:
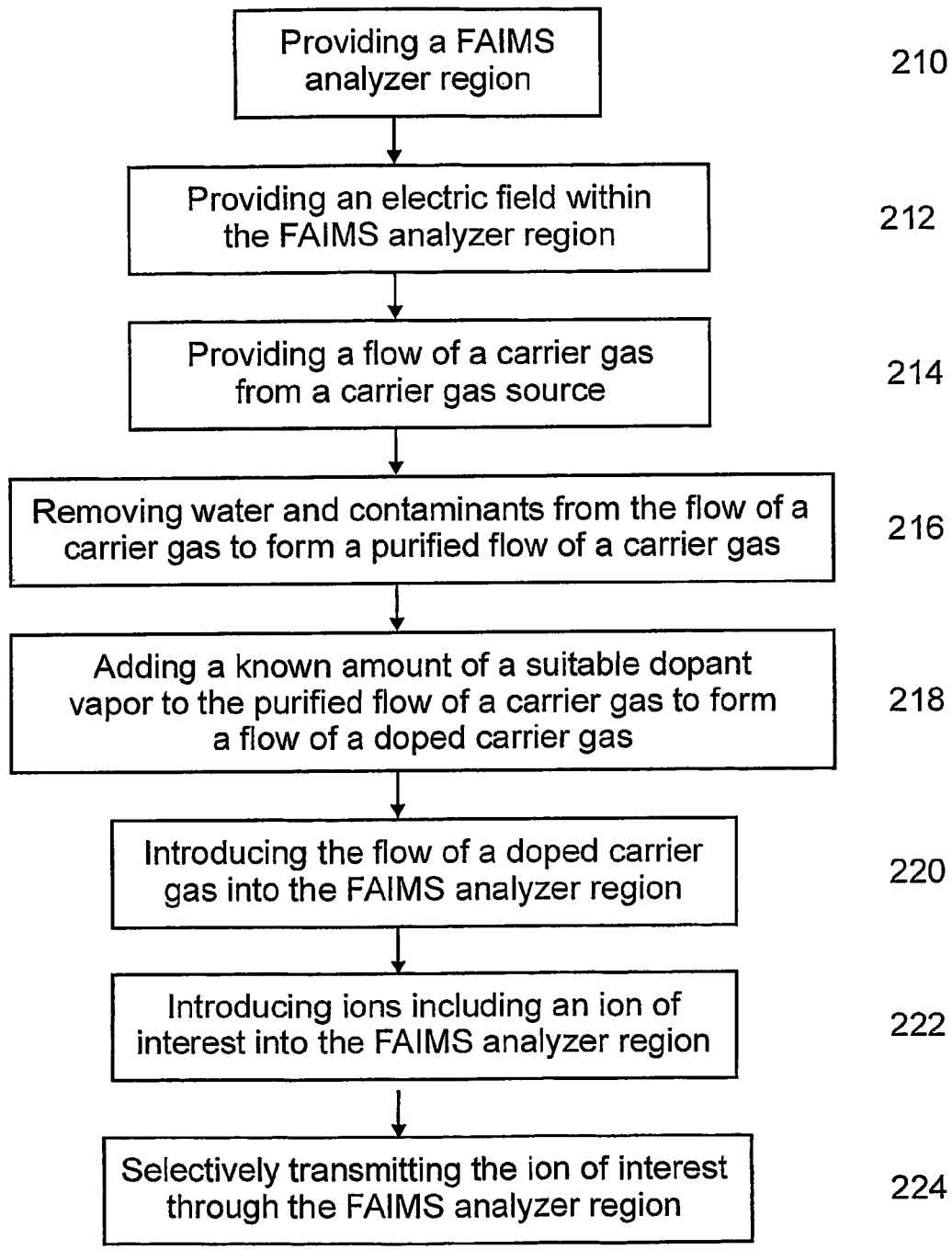
FIG. 15 is a simplified flow diagram for another method according to the instant invention of selectively transmitting ions within a FAIMS analyzer region using a carrier gas including a trace amount of an added component; and, FIG. 16 is a simplified flow diagram for yet another method according to the instant invention of selectively transmitting ions within a FAIMS analyzer region using a carrier gas including a trace amount of an added component.

Referring now to FIG. 15, shown a simplified flow diagram for another method according to the instant invention of selectively transmitting ions within a FAIMS analyzer region using a carrier gas including a trace amount of an added component, such as for instance a dopant gas. A FAIMS analyzer region defined by a space between two spaced-apart electrodes is provided at step 210. At step 212, an electric field is provided within the FAIMS analyzer region resulting from the application of an asymmetric waveform voltage to at least one of the two electrodes and from the application of a direct-current compensation voltage to at least one of the two electrodes. At step 214, a flow of a carrier gas is provided from a carrier gas source. The flow of a carrier gas is provided to a gas filter, such as for instance a charcoal/molecular sieve filter, to remove water and contaminants from the flow of a carrier gas at step 216, so as to obtain a flow of a purified carrier gas. At step 218 a trace amount of a predetermined dopant gas is added to the flow of a purified carrier gas to provide a flow of a doped carrier gas. At step 220, the flow of a doped carrier gas is introduced into the FAIMS analyzer region. Ions including an ion of interest are introduced into the FAIMS analyzer region at step 222, and at step 224 the ion of interest is selectively transmitted through the FAIMS analyzer region. Optionally, the method according to FIG. 15 includes a step of varying the trace amount of the predetermined dopant gas that is added to the flow of a purified carrier gas, so as to determine an optimal trace amount of the predetermined dopant gas.

Figure 16:
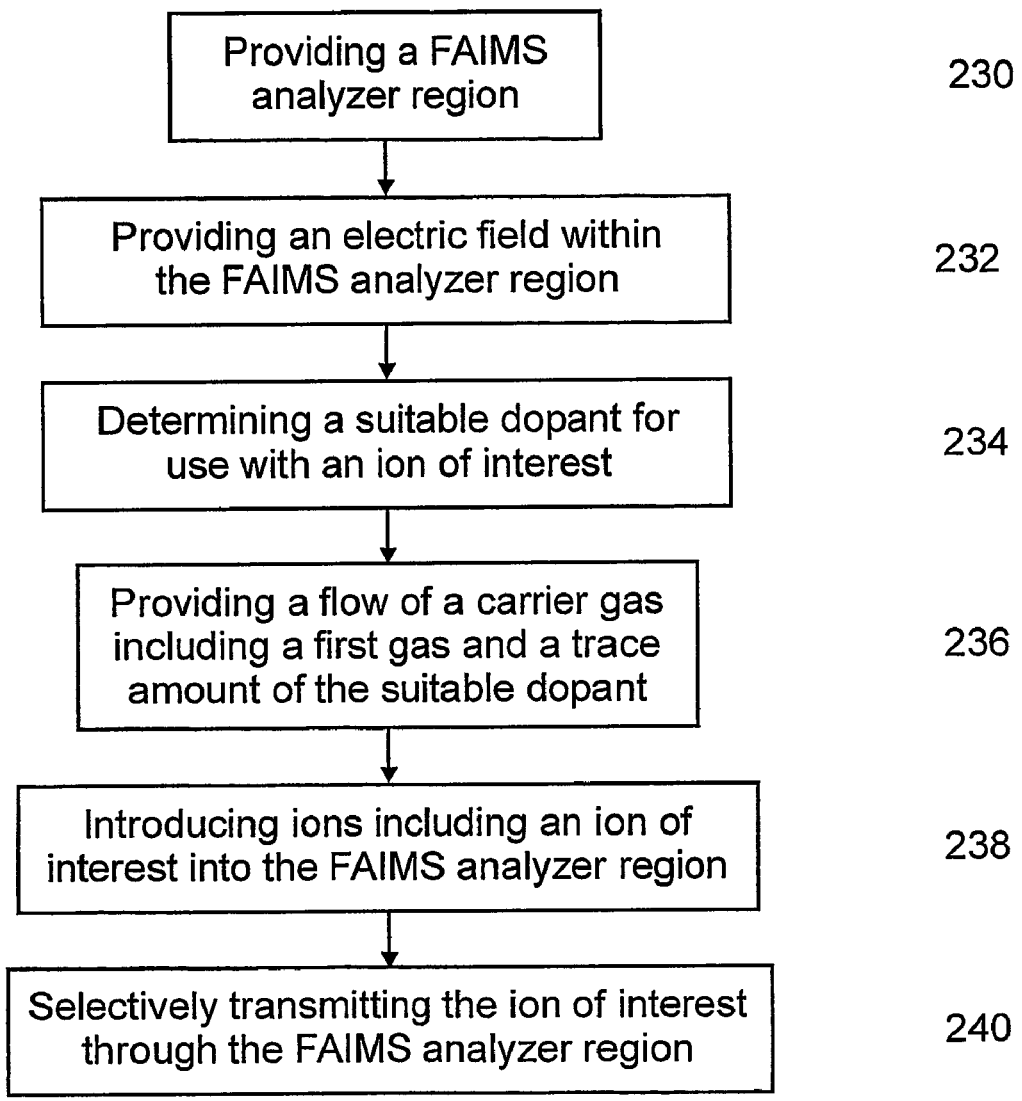

Referring now to FIG. 16, shown a simplified flow diagram for yet another method according to the instant invention of selectively transmitting ions within a FAIMS analyzer region using a carrier gas including a trace amount of an added component, such as for instance a dopant gas. A FAIMS analyzer region defined by a space between two spaced-apart electrodes is provided at step 230. At step 232, an electric field is provided within the FAIMS analyzer region resulting from the application of an asymmetric waveform voltage to at least one of the two electrodes and from the application of a direct-current compensation voltage to at least one of the two electrodes. At step 234 a suitable dopant gas is determined for improving at least one of a peak separation and a signal intensity relating to an ion of interest. At step 236, a flow of a carrier gas is provided through the FAIMS analyzer region, the carrier gas including a first gas and a trace amount of the suitable dopant gas. At step 238, ions including the ion of interest are introduced into the FAIMS analyzer region. At step 240, the ions of interest are selectively transmitted through the analyzer region.

The term dopant gas includes vapours produced by substances that are normally a liquid or a solid at standard temperature and pressure, as well as substances that are normally in the gaseous state at standard temperature and pressure. Optionally, the dopant gas is provided to the mixing chamber as an undiluted flow of the dopant gas, in particular a source of the dopant gas does not comprise another gas mixed with the dopant gas.

Numerous other embodiments may be envisaged without departing from the spirit and scope of the invention.

What is claimed is:

1. An apparatus for selectively transmitting ions comprising:
   a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting an ion of interest at a given combination of asymmetric waveform voltage and compensation voltage; and,
   a doping portion for receiving a flow of a carrier gas from a gas source and for controllably mixing a dopant gas with the flow of a carrier gas to produce a doped carrier gas stream containing a predetermined concentration of the dopant gas, the doping portion also in fluid communication with the analyzer region for providing the doped carrier gas stream thereto,
   wherein during use the doped carrier gas stream that is provided to the analyzer region contains less than 1% dopant gas by volume.

2. An apparatus according to claim 1, comprising a source of a dopant gas in fluid communication with the doping portion.

3. An apparatus according to claim 2, wherein the source of a dopant gas comprises a containing portion for containing a first gas mixture including up to approximately 1% dopant gas by volume.

4. An apparatus according to claim 2, wherein the source of a dopant gas comprises a containing portion for containing a first gas mixture including up to approximately 2500 ppm dopant gas.

5. An apparatus according to claim 1, wherein the doping portion is in fluid communication with a second gas source for providing a second separate flow of a carrier gas that, during use, is controllably mixed with the doped carrier gas flow prior to the doped carrier gas flow being introduced into the analyzer region, to provide a diluted doped carrier gas flow for introduction into the analyzer region.

6. An apparatus for selectively transmitting ions comprising:
   a high field asymmetric waveform ion mobility spectrometer comprising two electrodes defining an analyzer region therebetween, the two electrodes disposed in a spaced apart arrangement for allowing ions to propagate therebetween and for providing an electric field within the analyzer region resulting from the application of an asymmetric waveform voltage to at least one of the two electrodes and from the application of a compensation voltage to at least one of the two electrodes, for selectively transmitting an ion of interest at a given combination of asymmetric waveform voltage and compensation voltage;
   a carrier gas source for providing a flow of a carrier gas;
   a first containing portion for containing a first gas mixture including a first concentration of a dopant gas;
   a second containing portion for containing a second gas mixture including a second concentration of the dopant gas; and,
   a doping portion in fluid communication with the carrier gas source, the first containing portion, the second containing portion and the analyzer region, for receiving the flow of a carrier gas from the gas source and for controllably mixing at least one of the first gas mixture and the second gas mixture with the flow of the carrier gas, to form a doped carrier gas stream containing a predetermined concentration of the dopant gas, and for providing the doped carrier gas stream to the analyzer region,
   wherein during use the doped carrier gas stream that is provided to the analyzer region contains less than 1% dopant gas by volume.

7. An apparatus according to claim 6, wherein, during use, the first containing portion contains a first gas mixture including up to approximately 1% dopant gas by volume.

8. An apparatus according to claim 6, wherein, during use, the second containing portion contains a second gas mixture including between 0% dopant gas by volume and 1% dopant gas by volume.

9. An apparatus according to claim 6, wherein the doping portion comprises a flow selector for selectively mixing one or the other of the first gas mixture and the second gas mixture with the flow of a carrier gas.

10. An apparatus according to claim 6, wherein the doping portion comprises a flow combiner for mixing a controlled amount of the first gas mixture and a controlled amount of the second gas mixture with the flow of a carrier gas.

11. A method of selectively transmitting ions, comprising the steps of:
    introducing ions including an ion of interest into an analyzer region of a high field asymmetric waveform ion mobility spectrometer;
    providing a flow of a doped carrier gas other than air through the analyzer region, the doped carrier gas including a carrier gas and less than 10,000 ppm of a predetermined dopant gas, the predetermined dopant gas selected for improving at least one of a peak separation and a signal intensity relating to the ion of interest relative to the peak separation and the signal intensity relating to the ion of interest in the presence of the carrier gas only; and,
    selectively transmitting the ion of interest through the analyzer region in the presence of the doped carrier gas.

12. A method according to claim 11, wherein the predetermined dopant gas is water vapour.

13. A method according to claim 11, wherein the predetermined dopant gas is a vapour produced from an inorganic compound other than water.

14. A method according to claim 11, wherein the predetermined dopant gas is a vapour produced from an organic compound.

15. A method according to claim 14, wherein the organic compound is a halogenated compound.

16. A method according to claim 11, wherein the flow of a doped carrier gas comprises between 1 ppm and 10,000 ppm of the predetermined dopant gas.

17. A method according to claim 16 wherein the flow of a doped carrier gas comprises between 25 ppm and 1,000 ppm of the predetermined dopant gas.

18. A method according to claim 11, comprising the step of providing a flow of a second doped carrier gas through the analyzer region, the second doped carrier gas including a carrier gas and a trace amount of a second predetermined dopant gas, the second predetermined dopant gas selected for improving the other one of the at least one of a peak separation and a signal intensity relating to the ion of interest relative to the peak separation and the signal intensity relating to the ion of interest in the presence of the carrier gas only.

19. A method according to claim 11, comprising the step of varying the amount of the predetermined dopant gas to determine an optimal amount of the predetermined dopant gas for improving the at least one of a peak separation and a signal intensity relating to the ion of interest.

20. A method of selectively transmitting ions, comprising the steps of:
   providing an analyzer region defined by a space between two spaced-apart electrodes;
   providing an electric field within the analyzer region resulting from the application of an asymmetric waveform voltage to at least one of the two electrodes and from the application of a direct-current compensation voltage to at least one of the two electrodes;
   providing a flow of a carrier gas from a carrier gas source;
   removing water vapour from the flow of a carrier gas to provide a flow of a dried carrier gas;
   adding a trace amount of a predetermined dopant gas to the flow of a dried carrier gas to provide a flow of a doped carrier gas comprising less than 10,000 ppm of the predetermined dopant gas;
   introducing the flow of a doped carrier gas into the analyzer region;
   introducing ions including an ion of interest into the analyzer region; and,
   selectively transmitting the ion of interest through the analyzer region in the presence of the doped carrier gas.

21. A method according to claim 20, comprising the steps of:
   varying the applied compensation voltage to selectively transmit the ions of interest through the analyzer region in the presence of the flow of a dried carrier gas so as to obtain a first compensation voltage spectrum;
   obtaining a plurality of other compensation voltage spectra, each compensation voltage spectrum of the plurality of other compensation voltage spectra obtained by varying the applied compensation voltage to selectively transmit the ions of interest through the analyzer region in the presence of one of a plurality of a different dopant gases; and,
   selecting as the predetermined dopant gas one of the dopant gases of the plurality of different dopant gases on the basis of a difference between the compensation voltage spectrum obtained using the one of the dopant gases and the first compensation voltage spectrum.

22. A method according to claim 20, wherein the predetermined dopant gas is water vapour.

23. A method according to claim 20, wherein the predetermined dopant gas is a vapour produced from an inorganic compound other than water.

24. A method according to claim 20, wherein the predetermined dopant gas is a vapour produced from an organic compound.

25. A method according to claim 24, wherein the organic compound is a halogenated species.

26. A method according to claim 20, wherein the flow of a doped carrier gas comprises between 1 ppm and 10,000 ppm of the predetermined dopant gas.

27. A method according to claim 20, wherein the flow of a doped carrier gas comprises between 25 ppm and 1,000 ppm of the predetermined dopant gas.

28. A method according to claim 20, comprising the step of varying the trace amount of the predetermined dopant gas to determine an optimal trace amount of the predetermined dopant gas in the flow of a doped carrier gas.

29. A method of selectively transmitting ions, comprising the steps of:
   providing an analyzer region defined by a space between two spaced-apart electrodes;
   providing an electric field within the analyzer region resulting from the application of an asymmetric waveform voltage to at least one of the two electrodes and from the application of a direct-current compensation voltage to at least one of the two electrodes;
   determining a suitable dopant gas for improving one of a peak separation and a signal intensity relating to an ion of interest;
   providing a flow of a carrier gas other than air through the analyzer region, the carrier gas including a first gas and less than 10,000 ppm of the suitable dopant gas;
   introducing ions including the ion of interest into the analyzer region; and,
   selectively transmitting the ion of interest through the analyzer region.

30. A method according to claim 29, wherein the step of determining a suitable dopant gas includes a step of determining an optimal amount of the suitable dopant gas for improving the one of a peak separation and a signal intensity relating to the ion of interest.

31. A method according to claim 29, comprising the step of determining a suitable second dopant gas for improving the other one of a peak separation and a signal intensity relating to the ion of interest.

32. A method according to claim 31, wherein the step of determining a suitable second dopant gas includes a step of determining an optimal amount of the suitable second dopant gas for improving the other one of a peak separation and a signal intensity relating to the ion of interest.

33. A method according to claim 31, wherein one of the suitable dopant gas and the suitable second dopant gas is water vapour.

34. A method according to claim 31, wherein at least one of the suitable dopant gas and the suitable second dopant gas is a vapour produced from an inorganic compound other than water.

35. A method according to claim 31, wherein at least one of the suitable dopant gas and the suitable second dopant gas is a vapour produced from an organic compound.

36. A method according to claim 35, wherein the organic compound is a halogenated species.

37. A method according to claim 29, wherein the flow of a carrier gas comprises between 1 ppm and 10,000 ppm of the suitable dopant gas.

38. A method according to claim 29, wherein the flow of a doped carrier gas comprises between 25 ppm and 1,000 ppm of the suitable dopant gas.

* * * * *